(12) United States Patent
Ohyama et al.

(10) Patent No.: US 10,161,744 B2
(45) Date of Patent: Dec. 25, 2018

(54) THREE-DIMENSIONAL MEASUREMENT DEVICE

(71) Applicant: CKD Corporation, Aichi (JP)

(72) Inventors: Tsuyoshi Ohyama, Aichi (JP); Norihiko Sakaida, Aichi (JP); Takahiro Mamiya, Aichi (JP); Hiroyuki Ishigaki, Aichi (JP)

(73) Assignee: CKD Corporation, Aichi (JP)

( * ) Notice: Subject to any disclaimer, the term of this patent is extended or adjusted under 35 U.S.C. 154(b) by 0 days.

(21) Appl. No.: 15/849,911

(22) Filed: Dec. 21, 2017

(65) Prior Publication Data

US 2018/0112974 A1 Apr. 26, 2018

Related U.S. Application Data

(63) Continuation of application No. PCT/JP2016/050552, filed on Jan. 8, 2016.

(30) Foreign Application Priority Data

Jun. 23, 2015 (JP) .................................. 2015-125213

(51) Int. Cl.
*G01B 11/25* (2006.01)
*G06T 7/00* (2017.01)
(Continued)

(52) U.S. Cl.
CPC .......... *G01B 11/2513* (2013.01); *G01B 11/25* (2013.01); *G06T 7/001* (2013.01);
(Continued)

(58) Field of Classification Search
CPC ....... G01B 11/2513; G06T 7/001; G06T 7/60; G06T 2207/30152; G06T 2207/30141;
(Continued)

(56) References Cited

U.S. PATENT DOCUMENTS

| 5,848,188 A * | 12/1998 | Shibata ................ G01B 11/024 382/203 |
| 2010/0177192 A1* | 7/2010 | Ishigaki ................. G01B 11/25 348/135 |

(Continued)

FOREIGN PATENT DOCUMENTS

| JP | 2006-300539 A | 11/2006 |
| JP | 2009-115612 A | 5/2009 |

(Continued)

OTHER PUBLICATIONS

International Preliminary Report on Patentability issued in corresponding International Application No. PCT/JP2016/050552 dated Dec. 26, 2017 (11 pages).

(Continued)

*Primary Examiner* — Sang H Nguyen
(74) *Attorney, Agent, or Firm* — Osha Liang LLP

(57) ABSTRACT

A three-dimensional measurement device includes a light source and grid that irradiate a measurement object; a luminance controller that changes luminance levels of the light; a phase controller that changes phase levels of the light pattern; a camera that takes an image of the measurement object; and a processor that three-dimensionally measures a first measurement object area based on different image data taken by radiating a first light pattern in different phases; determines a relationship between a gain and offset determined according to an imaging condition based on the different image data; and three-dimensionally measures a second measurement object area based on two different image data taken by radiating a second light pattern in two different phases by using a gain and offset regarding each pixel determined according to a luminance value of each pixel in the two different image data and the determined relationship.

20 Claims, 11 Drawing Sheets

(51) Int. Cl.
   *G06T 7/60* (2017.01)
   *G06T 7/521* (2017.01)
(52) U.S. Cl.
   CPC .............. *G06T 7/521* (2017.01); *G06T 7/60* (2013.01); *G06T 2200/04* (2013.01); *G06T 2207/10152* (2013.01); *G06T 2207/30141* (2013.01); *G06T 2207/30148* (2013.01); *G06T 2207/30152* (2013.01)
(58) Field of Classification Search
   CPC . G06T 2207/30148; G06T 2207/10152; G06T 2200/04
   See application file for complete search history.

(56) References Cited

U.S. PATENT DOCUMENTS

| | | | | |
|---|---|---|---|---|
| 2010/0183194 | A1* | 7/2010 | Umemura | G01B 11/03 382/103 |
| 2014/0071243 | A1* | 3/2014 | Nakatsukasa | G01B 11/25 348/46 |
| 2017/0370708 | A1* | 12/2017 | Fujiwara | G01B 11/25 |

FOREIGN PATENT DOCUMENTS

| | | |
|---|---|---|
| JP | 2010-243438 A | 10/2010 |
| JP | 2012-053015 A | 3/2012 |

OTHER PUBLICATIONS

International Search Report issued in corresponding International Application No. PCT/JP2016/050552 dated Mar. 22, 2016 (5 pages).

\* cited by examiner

FIG. 4A

SOLDERING TABLE

| TYPE OF SOLDER | LUMINANCE |
|---|---|
| a COMPANY | △ △ △ |
| b COMPANY | □ □ □ |
| c COMPANY | × × × |
| ⋮ | ⋮ |

SUBSTRATE TABLE

| TYPE OF SUBSTRATE | LUMINANCE |
|---|---|
| GREEN | ▲ ▲ ▲ |
| BLUE | ■ ■ ■ |
| BLACK | ○ ○ ○ |
| ⋮ | ⋮ |

~27B

THREE-DIMENSIONAL MEASUREMENT DEVICE

BACKGROUND OF THE INVENTION

Technical Field

The present disclosure relates to a three-dimensional measurement device for three-dimensional measurement using the phase shift method.

Background

In general, a printed circuit board includes an electrode pattern that is provided on a base substrate made of a glass epoxy resin and a resist film that is placed to protect the surface of the printed circuit board. When electronic components are to be mounted on this printed circuit board, solder paste is first printed at predetermined positions on the electrode pattern without protection of the resist film. The electronic components are then temporarily fastened on the printed circuit board by means of the viscosity of the solder paste. The printed circuit board is then introduced into a reflow furnace and is subjected to a predetermined reflow process that achieves soldering. Recently there has been a need to inspect the printing condition of solder paste in a stage prior to introduction into the reflow furnace. A three-dimensional measurement device may be used for this inspection.

In a three-dimensional measurement device using the phase shift method, a measurement object (printed circuit board in this case) is irradiated with a light pattern emitted from an irradiator configured by a combination of a light source configured to emit a predetermined light and a grid configured to convert the light emitted from the light source into a light pattern having a sinusoidal (striped) light intensity distribution. Points on the substrate are observed with an imaging unit placed immediately above the substrate. The imaging unit may be, for example, a CCD camera including a lens, an imaging element and the like.

In the configuration described above, intensity (luminance) I of the light at each coordinates (pixel) on image data taken by the imaging unit is given by Expression (T1) given below:

$$I = f \cdot \sin \varphi + e \quad (T1)$$

where f denotes a gain, e denotes an offset and $\varphi$ denotes a phase of the light pattern.

The phase of the light pattern is changed in, for example four different stages ($\varphi+0$, $\varphi+90°$, $\varphi+180°$ and $\varphi+270°$) by changeover control of the above grid, and image data having intensity distributions I0, I1, I2 and I3 corresponding to these phases is taken. The phase $\varphi$ is determined by cancelling out f (gain) and e (offset) according to Expression (T2) given below:

$$\varphi = \tan^{-1} [(I_1 - I_3)/(I_2 - I_0)] \quad (T2)$$

A height (Z) at each coordinates (X,Y) on a measurement object is determined by using this phase $\varphi$, based on the principle of triangulation.

The periphery (hereinafter referred to as background area) of a printed portion of solder paste on the printed circuit board may be in various colors. This is because various colors are used for the glass epoxy resin and the resist film. In a background area of a relatively dark color such as black, image data taken by the imaging unit has a small contrast. In other words, the image data has a small difference between light and dark of light pattern (small luminance difference). This may make it difficult to perform height measurement of the background area. With a view to measuring the height of the solder paste printed on a substrate with the higher accuracy, it is originally desirable to set a height reference in the substrate. The background area is, however, not appropriately usable as the height reference surface. As a result, the height reference cannot be set in the substrate.

By taking into account the foregoing, a three-dimensional measurement device has been recently proposed to perform measurement using two different light patterns of different luminance levels (as described in, for example, Patent Literature 1). More specifically, the proposed three-dimensional measurement device performs three-dimensional measurement of an inspection object area (solder area) on the printed circuit board, based on image data obtained by radiation of a light pattern of a first luminance and perform three-dimensional measurement of a measurement reference area (background area) on the printed circuit board, based on image data obtained by radiation of a light pattern of a second luminance. The three-dimensional measurement device then measures the height or the volume of solder paste in the inspection object area using the measurement reference area as the height reference surface.

CITATION LIST

Patent Literature

PTL 1: JP 2006-300539A

SUMMARY OF THE INVENTION

In the prior art three-dimensional measurement device using the phase shift method, however, there is a need to change the phase of the radiated light pattern in four different stages (or three different stages) and to take four different (or three different) images.

In the case of measurement with changing over two different light patterns of different luminance levels, the procedure first radiates a first light pattern of a first luminance, changes the phase of the first light pattern in four different stages (or in three different stages) and takes four different (or three different) images under the first light pattern of the different phases. The procedure subsequently changes the luminance, radiates a second light pattern of a second luminance, changes the phase of the second light pattern in four different stages three different stages) and takes four different (or three different) images under the second light pattern of the different phases. This requires a total of eight (or six) imaging operations, four (or three) imaging operations under the light pattern of each luminance. This may significantly increase the imaging time.

When a large number of measurement object areas are set on a single printed circuit board a several-fold time period is required for measurement of the single printed circuit board. There is accordingly a need for further shortening the measurement time.

Those needs exist in the field of not only height measurement of, for example, the solder paste printed on the printed circuit board but other three-dimensional measurement devices.

By taking into account the circumstances described above, one or more embodiments of the invention provide a three-dimensional measurement device that achieves highly accurate and time efficient three-dimensional measurement with the phase shift method.

The following describes each of various aspects provided adequately to solve the problems described above. Functions and advantageous effects that are characteristic of each of the aspects are also described as appropriate.

Aspect 1. There is provided a three-dimensional measurement device comprising an irradiator configured to include a light source that emits a predetermined light and a grid that converts the light from the light source into a light pattern having a striped light intensity distribution, and to irradiate a measurement object including at least a first measurement object area and a second measurement object area with the light pattern; a luminance controller configured to change a luminance of the light emitted from the light source; a phase controller configured to control transfer or changeover of the grid and to change a phase of the light pattern radiated from the irradiator in a plurality of phase levels; an imaging unit configured to take an image of reflected light from the measurement object irradiated with the light pattern; and an image processor configured to perform three-dimensional measurement of the measurement object by a phase shift method, based on image data taken by the imaging unit. The image processor comprises a first measurement unit configured to perform three-dimensional measurement of the first measurement object area, based on a predetermined number of different image data taken by radiating a first light pattern of a first luminance corresponding to the first measurement object area in a predetermined number of different phases; a relationship grasping unit configured to grasp a relationship between a gain and an offset determined according to a predetermined imaging condition, based on the predetermined number of different image data taken under the first light pattern; and a second measurement unit configured to perform three-dimensional measurement of the second measurement object area, based on two different image data taken by radiating a second light pattern of a second luminance corresponding to the second measurement object area in two different phases by using values of a gain and an offset with respect to each pixel determined according to a luminance value of each pixel in the two different image data and the relationship between the gain and the offset grasped by the relationship grasping unit.

The "first luminance corresponding to the first measurement object area" and the "second luminance corresponding to the second measurement object area" may be set in advance or may be determined at every time of separate measurement. In the case of a known "first luminance corresponding to the first measurement object area," the "first luminance corresponding to the first measurement object area" may be set in advance, and the "second luminance corresponding to the second measurement object area" may be determined, based on image data with the "first luminance corresponding to the first measurement object area."

As described above, according to the prior art technique, in imaging for the purpose of measurement of the first measurement object area (for example, solder area), the second measurement object area (for example, background area) of the image data is likely to have an excessively high luminance, an excessively low luminance or a small difference between light and dark (small luminance difference). This is likely to cause a significant decrease in measurement accuracy with regard to the second measurement object area.

The above aspect 1 is configured to perform three-dimensional measurement of the first measurement object area (for example, light portion of a relatively high brightness), based on the image data taken with radiation of the first light pattern of the first luminance corresponding to the first measurement object area and to perform three-dimensional measurement of the second measurement object area (for example, dark portion of a relatively low brightness), based on the image data taken with radiation of the second light pattern of the second luminance corresponding to the second measurement object area. This configuration allows for three-dimensional measurement of both the first measurement object area and the second measurement object area, based on image data taken under the light patterns of the respectively different and adequate luminance levels. This results in suppressing a decrease in measurement accuracy.

Additionally, this aspect is configured to grasp the relationship between the gain A and the offset B (for example, A=K (proportional constant)×B) that is determined according to the predetermined imaging condition, based on the predetermined number of image data taken for the purpose of measurement of the first measurement object area.

The configuration of this aspect allows for three-dimensional measurement at measurement object coordinates (x,y) by the phase shift method, based on two different image data taken under a light pattern that changes the phase in two different phase levels, by using the relationship between the gain A and the offset B of the light pattern that is determined according to the predetermined imaging condition and the value of a gain A(x,y) or an offset B(x,y) of the light pattern at the measurement object coordinates (x,y) that is determined from a luminance value V(x,y) of the measurement object coordinates (x,y) of the image data.

The configuration of this aspect accordingly enables three-dimensional measurement of the second measurement object area by the phase shift method to be performed by simply obtaining two different image data taken under the second light pattern a changes the phase in at least two different phase levels.

For example, when four different (or three different) images are taken with radiation of the first light pattern of the first luminance in four different (or three different) phases and two different images are subsequently taken with radiation of the second light pattern of the second luminance in two different phases, the total number of imaging operations is six times (or five times). This significantly decreases the imaging time.

Compared with the prior art technique that performs three-dimensional measurement with regard to different areas on a measurement object with changing the luminance of the light pattern, the configuration of this aspect requires a smaller total number of imaging operations and thereby shortens the imaging time. This results in remarkably shortening the measurement time.

The light emitted from the light source is attenuated when passing through the grid, is subsequently attenuated when being reflected by the measurement object, is lastly attenuated during A/D conversion (along to digital conversion) in the imaging unit, and is then obtained as a luminance value of each pixel in the image data.

The luminance value of each pixel in the image data taken by the imaging unit may thus be expressed by, for example, multiplying the luminance of the light source, the attenuation rate when the light emitted from the light source passes through the grid, the reflectance when the light is reflected by the measurement object and the conversion efficiency during A/D conversion (analog to digital conversion) in the imaging unit.

For example, a luminance of the light source (uniform light) is represented by and a transmittance of the grid is expressed as $G=\alpha \sin \theta + \beta$ where $\alpha$ and $\beta$ denote arbitrary constants.

A reflectance at coordinates (x,y) of the measurement object is represented by R(x,y); a conversion efficiency of each pixel of the imaging unit (imaging element) is represented by E; a luminance value of a pixel on an image corresponding to the coordinates (x,y) on the measurement object is represented by V(x,y); a gain of the light pattern at the coordinates (x,y) on the measurement object is represented by A(x,y); and an offset of the light pattern at the coordinates (x,y) on the measurement object is represented by B(x,y). In this case, the luminance value of each pixel may be expressed by Expression (F1) given below:

[Math. 1]

$$V(x,y) = L \times G \times R(x,y) \times E \qquad (F1)$$
$$= A(x,y)\sin\theta + B(x,y)$$

The gain A(x,y) may be expressed by a difference between a luminance value $V(x,y)_{MAX}$ with light of "sin $\theta=1$" and a luminance value $V(x,y)_{MIN}$ with light of "sin $\theta=-1$." For example, when a transmittance of the grid at $\theta=0$ (=average transmittance) is represented by $G\theta_{=0}$, a transmittance of the grid at $\theta=\pi/2$ (=maximum transmittance) is represented by $G\theta_{=\pi/2}$, and a transmittance of the grid at $\theta=-\pi/2$ (=minimum transmittance) represented by $G\theta_{=-\pi/2}$, the gain A(x,y) may be expressed by Expression (F2) given below:

[Math. 2]

$$A(x,y) = \{(L \times G_{\theta=\pi/2} \times R(x,y) \times E) - \qquad (F2)$$
$$(L \times G_{\theta=-\pi/2} \times R(x,y) \times E)\}/2$$
$$= \{(L \times R(x,y) \times E) \times (G_{\theta=\pi/2} - G_{\theta=-\pi/2})\}/2$$

The offset B(x,y) is equal to a luminance value V(x,y) with light of "sin $\theta=0$" and is an average value of the luminance value $V(x,y)_{MAX}$ with the light of "sin $\theta=1$" and the luminance value $V(x,y)_{MIN}$ with the light of "sin $\theta=-1$." The offset B(x,y) may be expressed by Expression (F3) given below:

[Math. 3]

$$B(x,y) = L \times G_{\theta=0} \times R(x,y) \times E \qquad (F3)$$
$$= \{(L \times G_{\theta=\pi/2} \times R(x,y) \times E) +$$
$$(L \times G_{\theta=-\pi/2} \times R(x,y) \times E)\}/2$$
$$= \{(L \times R(x,y) \times E) \times (G_{\theta=\pi/2} - G_{\theta=-\pi/2})\}/2$$

The maximum value $V(x,y)_{MAX}$, the minimum value $V(x,y)_{MIN}$ and the average value $V(x,y)_{AV}$ may be respectively expressed by Expressions (F4), (F5) and (F6) given below and provide such a relationship as that shown in the graph of FIG. 11.

[Math. 4]

$$V(x,y)_{MAX}=(L \times G_{\theta=\pi/2} \times R(x,y) \times E)=B(x,y)+A(x,y) \qquad (F4)$$

$$V(x,y)_{MIN}=(L \times G_{\theta=-\pi/2} \times R(x,y) \times E)=B(x,y)+A(x,y) \qquad (F5)$$

$$V(x,y)_{AV}=(L \times R(x,y) \times E \times (G_{\theta=\pi/2}+G_{\theta=-\pi/2})/2=B(x,y) \qquad (F6)$$

As understood from FIG. 11, the average value $V(x,y)_{AV}$ of the maximum value $V(x,y)_{MAX}$ of the luminance value and the minimum value $V(x,y)_{MIN}$ of the luminance value at predetermined coordinates (x,y) is equal to the offset B(x,y). The difference between the offset B(x,y) and the maximum value $V(x,y)_{MAX}$ and the difference between the offset B(x,y) and the minimum value $V(x,y)_{MIN}$ are respectively given as the gain A(x,y).

The luminance value V(x,y) changes in proportion to the luminance L or the reflectance R(x,y) of the light source. The value of the gain A or the offset B is accordingly halved, for example, at a coordinate position having half the reflectance R.

Expression (F7) given below is derived by substituting Expressions (F2) and (F3) given above with Expressions (F2') and (F3') given below and collectively reorganizing these Expressions (F2') and (F3'):

[Math. 5]

$$2A(x,y)/(G_{\theta=\pi/2}-G_{\theta=-\pi/2})=(L \times R(x,y) \times E) \qquad (F2')$$

$$2B(x,y)/(G_{\theta=\pi/2}-G_{\theta=-\pi/2})=(L \times R(x,y) \times E) \qquad (F3')$$

$$2A(x,y)/(G_{\theta=\pi/2}-G_{\theta=-\pi/2})=2B(x,y)/(G_{\theta=\pi/2}-G_{\theta=-\pi/2}) \qquad (F7)$$

Additionally, Expression (F8) given below is derived by solving Expression (F7) given above with regard to A(x,y) and is expressed as shown in the graph of FIG. 12:

[Math. 6]

$$A(x,y) = B(x,y) \times (G_{\theta=\pi/2} - G_{\theta=-\pi/2})/(G_{\theta=\pi/2}+G_{0=-\pi/2}) \qquad (F8)$$
$$= K \times B(x,y)$$

where proportional constant
$$K = (G_{\theta=\pi/2} - G_{\theta=-\pi/2})/(G_{\theta=\pi/2}+G_{\theta=-\pi/2})_o$$

Changing one of the luminance L and the reflectance R(x,y) of the light source while fixing the other increases or decreases the offset B(x,y) and also increases or decreases the gain A(x,y) in proportion to the offset B(x,y). According to this Expression (F8), the other of the gain A and the offset B is determinable by determining one of the gain A and the offset B. The proportional constant K is determined according to the transmittance G of the grid, independently of the luminance L and the reflectance R of the light source. This may be expressed as Aspects 2 and 3 described below.

Changing the luminance L of the light source (for example, changing from the first luminance to the second luminance) changes the luminance value V(x,y) at the measurement object coordinates (x,y) on the image data, i.e., the values of the gain A(x,y) and the offset B(x,y) of the light pattern at the measurement object coordinates (x,y), while keeping unchanged the proportional constant K that does not depend on the luminance L of the light source. Accordingly, the first light pattern and the second light pattern emitted by using the same grid have different values of the gain A and the offset B but keep the proportional constant K unchanged.

A configuration of irradiating a measurement object simultaneously with a plurality of light patterns of different phases at different wavelengths (with regard to RGB components) enables three different image data having different phases to be obtained by one imaging operation. In this configuration, however, the respective light patterns of the RGB components have, for example, different luminance levels of the light source, different reflectance levels at the measurement object, different transmittances of the grid, and different conversion efficiencies of the imaging element and accordingly have different values of the gain A and the offset B with regard to the respective light patterns of the RGB components. In three-dimensional measurement by the phase shift method based on the three different image data obtained by one imaging operation, calculation is performed with ignoring the errors on the assumption that the respective light patterns of the RGB components provide the same values of the gain A and the offset B. This is likely to cause a significant decrease in measurement accuracy. The configuration of Aspect 1, on the other hand, enables a plurality of image data having different phases to be obtained without causing differences in the gain A and the offset B. This accordingly suppresses a decrease in measurement accuracy.

Aspect 2: In the three-dimensional measurement device described in Aspect 1 above, the relationship between the gain and the offset may be a relationship that mutually unequivocally determines the gain and the offset.

When the relationship between the gain A and the offset B is a relationship that mutually unequivocally determines the gain A and the offset B, the offset B may be determinable according to the gain A or the gain A may be determinable according to the offset B by referring to, for example, a numerical table or table data provided to indicate the relationship between the gain A and the offset B.

Aspect 3: In the three-dimensional measurement device described in Aspect 1 above, the relationship between the gain and the offset may be a relationship that gives the gain and the offset proportional to each other.

When the relationship between the gain and the offset is a relationship that gives the gain and the offset proportional to each other, the offset B may be determinable according to the gain A or the gain A may be determinable according to the offset B by referring to, for example, a relational expression such as A=K×B (where K denotes a proportional constant). This may be implemented by such a configuration as that of Aspect 4 described below.

Aspect 4: In the three-dimensional measurement device described in any of Aspects 1 to 3 above, the second measurement unit may calculate a phase θ that satisfies relations of Expressions (1), (2) and (3) given below in measurement of the second measurement object area:

$$V_0 = A \sin\theta + B \quad (1)$$

$$V_1 = A \sin(\theta+\gamma) + B \quad (2)$$

$$A = KB \quad (3)$$

where $V_0$ and $V_1$ respectively denote luminance values of each pixel in the two different image data when the second light pattern changes the phase in the two different phases that are respectively expressed as relative phases of 0 and γ, γ≠0, A denotes the gain, B denotes the offset and K denotes a proportional constant.

In the above configuration of Aspect 4, Expression (4) given below is derived by substituting Expression (3) given above into Expression (1) given above:

$$V_0 = KB \sin\theta + B \quad (4)$$

Expression given below is derived by solving Expression (4) with regard to the offset B:

$$B = V_0/(K \sin\theta + 1) \quad (5)$$

Expression (6) given below is derived by substituting Expression (3) given above into Expression (2) given above:

$$V_1 = KB \sin(\theta+\gamma) + B \quad (6)$$

Expression (7) given below is derived by substituting Expression (6) given above into Expression (5) given above and reorganizing the expression as shown by [Math. 7] given below.

[Math. 7]

$$\begin{aligned}V_1 &= K \times \{V_0/(K\sin\theta+1)\}\sin(\theta+\gamma) + \{V_0/(K\sin\theta+1)\} \quad (7)\\ V_1 \times (K\sin\theta+1) &= KV_0\sin(\theta+\gamma) + V_0 \\ &= KV_0\{\sin\theta\cos\gamma + \sin\gamma\cos\theta\} + V_0 \\ -V_1 K\sin\theta + KV_0\cos\gamma\sin\theta &+ KV_0\sin\gamma\cos\theta + V_0 - V_1 = 0 \\ K(V_0\cos\gamma - V_1)\sin\theta &+ KV_0\sin\gamma\cos\theta + (V_0 + V_1) = 0 \\ (V_0\cos\gamma - V_1)\sin\theta &+ V_0\sin\gamma\cos\theta + (V_0 - V_1)/K = 0\end{aligned}$$

Expression (7) given above ay be rewritten as Expression (8) given below "$V_0 \cos\gamma - V_1 = a$," "$V_0 \sin\gamma = b$" and "$(V_0 - V_1)/K = c$":

$$a \sin\theta + b \cos\theta + c = 0 \quad (8)$$

Expression (9) shown by [Math. 9] given below is derived by solving Expression (8) given above with regard to the phase θ as shown by [Math. 8] given below:

[Math. 8]

$$\frac{a}{b}\sin\theta + \sqrt{1-\sin^2\theta} + \frac{c}{b} = 0$$

$$\sqrt{1-\sin^2\theta} += \frac{1}{b}(c + a\sin\theta)$$

$$1 - \sin^2\theta = \frac{1}{b^2}(c^2 + 2ac\sin\theta + a^2\sin^2\theta)$$

$$b^2 - b^2\sin^2\theta = c^2 + 2ac\sin\theta + a^2\sin^2\theta$$

$$(a^2 + b^2)\sin^2\theta + 2ac\sin\theta + c^2 = 0$$

$$\sin\theta = \frac{-ac \pm \sqrt{a^2c^2 - (a^2+b^2)(c^2-b^2)}}{a^2+b^2}$$

$$\theta = \sin\theta\left[\frac{-ac \pm \sqrt{a^2c^2 - (a^2+b^2)(c^2-b^2)}}{a^2+b^2}\right]$$

[Math. 9]

$$\theta = \sin^{-1}\left[\frac{-ac \pm b\sqrt{a^2+b^2-c^2}}{a^2+b^2}\right] \quad (9)$$

where
$a = V_0\cos\gamma - V_1$
$b = V_0\sin\gamma$
$c = (V_0 - V_1)/K$

The configuration of "calculating the phase θ that satisfies relations of Expressions (1), (2) and (3)" in Aspect 4 described above may thus be regarded as the configuration of "calculating the phase θ according to Expression (9)." The algorithm for obtaining the phase θ is not necessarily limited to Expression (9) given above, but any other configuration that satisfies the relations of Expressions (1), (2) and (3) given above may be employed.

Aspect 5: In the three-dimensional measurement device described in Aspect 4 above, γ may be equal to 180 degrees.

The configuration of this Aspect 5 causes two imaging operations to be performed under the second light pattern of two different phases that differ by 180 degrees.

Expression (10) given below is derived by substituting γ=180 degrees in Expression (2) given above:

$$V_1 = A\sin(\theta + 180°) + B \qquad (10)$$
$$= -A\sin\theta + B$$

Expression (11) given below is derived from Expressions (1) and (10) given above, and Expression (12) given below is derived by solving Expression (11) with regard to the offset B:

$$V_0 + V_1 = 2B \qquad (11)$$

$$B = (V_0 + V_1)/2 \qquad (12)$$

Additionally, Expression (13) given below is derived by substituting Expression (12) given above into Expression (3) given above:

$$A = KB \qquad (13)$$
$$= K(V_0 + V_1)/2$$

Expression (1') given below is obtained by rearranging Expression (1) given above with regard to "sin θ":

$$\sin\theta = (V_0 - B)/A \qquad (1')$$

Expression (14) given below is derived by substituting Expressions and (13) given above into Expression (1') given above:

$$\sin\theta = \{V_0 - (V_0 + V_1)/2\}/\{K(V_0 + V_1)/2\} \qquad (14)$$
$$= (V_0 - V_1)/K(V_0 + V_1)$$

Expression (15) given below is derived by solving Expression (14) given above with regard to the phase θ:

$$\theta = \sin^{-1}[(V_0 - V_1)/K(V_0 + V_1)] \qquad (15)$$

The phase θ may thus be specified by the known luminance values $V_0$ and $V_1$ and the constant K.

As described above, the above configuration of Aspect 5 enables the phase θ to be determined by a relatively simple arithmetic expression and further increases the processing speed in three-dimensional measurement of the measurement object.

Aspect 6: In the three-dimensional measurement device described in Aspect 4 above, γ may be equal to 90 degrees.

The configuration of this Aspect 6 causes two imaging operations to be performed under the second light pattern of two different phases that differ by 90 degrees.

Expression (16) given below is derived by substituting γ=90 degrees in Expression (2) given above:

$$V_1 = A\sin(\theta + 90°) + B \qquad (16)$$
$$= A\cos\theta + B$$

Expression (17) given below is derived by rearranging Expression (16) given above with regard to "cos θ":

$$\cos\theta = (V_1 - B)/A \qquad (17)$$

As described above, Expression (1') given below is obtained by rearranging Expression (1) given above with regard to "sin θ":

$$\sin\theta = (V_0 - B)/A \qquad (1')$$

Expression (19) given below is derived by substituting Expressions (1') and (17) given above into Expression (18) given below, and Expression (20) given below is derived by rearranging this Expression (19):

$$\sin^2\theta + \cos^2\theta = 1 \qquad (18)$$

$$\{(V_0 - B)/A\}^2 + \{(V_1 - B)/A\}^2 = 1 \qquad (19)$$

$$(V_0 - B)^2 + (V_1 - B)^2 = A^2 \qquad (20)$$

Expression (21) given below is derived by substituting Expression (3) given above into Expression (20) given above, and Expression (22) given below is derived by rearranging this Expression (21):

$$(V_0 - B)^2 + (V_1 - B)^2 = K^2 B^2 \qquad (21)$$

$$(2 - K^2)B^2 - 2(V_0 + V_1)B + V_0^2 + V_1^2 = 0 \qquad (22)$$

Expression (23) given below is derived by solving Expression (22) given above with regard to the offset B:

[Math. 10]

$$B = (V_0 + V_1) \pm \sqrt{(V_0 + V_1)^2 - (2 - K^2)V_0^2 V_1^2} \qquad (23)$$

where B>0

The offset B may thus be specified by the known luminance values $V_0$ and $V_1$ and the constant K.

Expression (25) given below is derived by substituting Expressions (1') and (17) given above into Expression (24) given below, and Expression (26) given below is derived by rearranging this Expression (25):

$$\tan\theta = \sin\theta/\cos\theta \qquad (24)$$
$$= \{(V_0 - B)/A\}/\{(V_1 - B)/A\} \qquad (25)$$
$$= (V_0 - B)/(V_1 - B) \qquad (26)$$

Expression (27) given below is derived by solving Expression (26) given above with regard to the phase θ:

$$\theta = \tan^{-1}\{(V_0 - B)/(V_1 - B)\} \qquad (27)$$

The phase θ may thus be specified by the known luminance values $V_0$ and $V_1$ and the constant K according to Expression (23) given above.

As described above, the above configuration of Aspect 6 enables the phase θ to be determined by an arithmetic expression using "$\tan^{-1}$." This allows for measurement of the height in the range of 360 degrees from −180 degrees to 180 degrees and further expands the measurement range.

Aspect 7: in the three-dimensional measurement device described in any of Aspects 1 to 6 above, one of the first measurement object area and the second measurement object area may be an inspection object area, and the other may be a measurement reference area.

This configuration of Aspect 7 ensures more appropriate measurement of the inspection object area using the measurement reference area as the reference surface and thereby enhances the measurement accuracy. However, the first measurement object area subjected to the greater number of imaging operations may be the "inspection object area," in order to further enhance the measurement accuracy of the "inspection object area."

Aspect 8: In the three-dimensional measurement device described in any of Aspects 1 to 7 above, the measurement object may be either a printed circuit board with solder paste printed thereon or a wafer substrate with a solder bump formed thereon.

This configuration of Aspect 8 allows for measurement of the height of, for example, the solder paste printed on the printed circuit board or the solder bump formed on the wafer substrate. This configuration also enables the good/poor quality of the solder paste or the solder bump to be determined, based on the measurement value in inspection of the solder paste or the solder bump. This configuration accordingly ensures the functions and the advantageous effects of the respective aspects described above in this inspection and allows for the good/poor quality determination with high accuracy. This results in improving the inspection accuracy in a solder printing inspection apparatus or in a solder bump inspection apparatus.

For example, when the measurement object is a printed circuit board, the above "inspection object area (for example, first measurement object area)" may be a "solder area" in which solder paste is printed. The "measurement reference area (for example, second measurement object area)" may be a "background area" other than the solder area. The "background area" may be, for example, a portion where an electrode pattern is exposed without printing solder paste, a portion where a base substrate made of, for example, a glass epoxy resin, is exposed, a portion of a resist film placed to coat the electrode pattern a portion of a resist film placed to coat the base substrate.

BRIEF DESCRIPTION OF THE DRAWINGS

FIG. 4A is a diagram illustrating a soldering table according to one or more embodiments of the invention;

FIG. 4B is a diagram illustrating a substrate table according to one or more embodiments of the invention;

DETAILED DESCRIPTION

The following describes one embodiment with reference to the drawings. The configuration of a printed circuit board as an object to be measured that is an inspection object is described first in detail.

Figure 2:
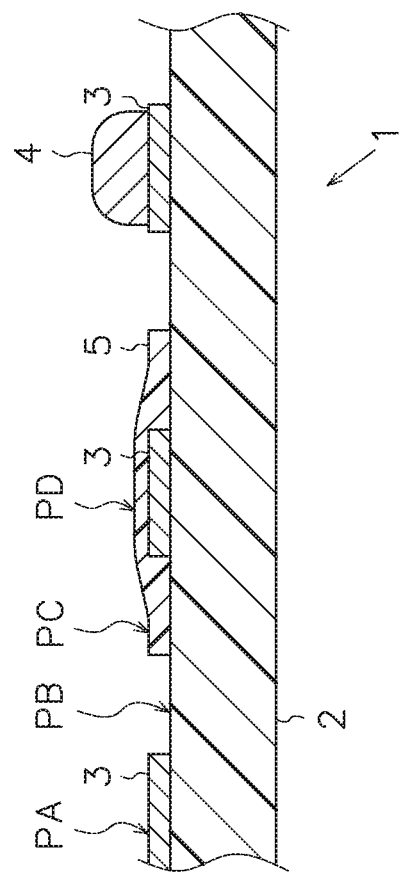
FIG. 2 is a partial enlarged sectional view illustrating a printed circuit board according to one or more embodiments of the invention.

As shown in FIG. 2, the printed circuit board 1 includes an electrode pattern 3 made of copper foil and provided on a flat plate-like base substrate 2 that is made of, for example, a glass/epoxy resin. Solder paste 4 is further printed on the predetermined electrode pattern 3.

Hereinafter, an area where this solder paste 4 is printed is called "solder area." A remaining part other than the solder area is generally called "background area." This background area includes an area where the electrode pattern 3 is exposed (shown by a symbol PA), an area where the base substrate 2 is exposed (shown by a symbol PB), an area where a resist film 5 is placed to coat on the base substrate 2 (shown by a symbol PC), and an area where a resist film 5 is placed to coat the electrode pattern 3 (shown by a symbol PD). The surface of the printed circuit board 1 is coated with the resist film 5, in order to prevent the solder paste 4 from being mounted on any part other than a predetermined wiring part.

Figure 1:
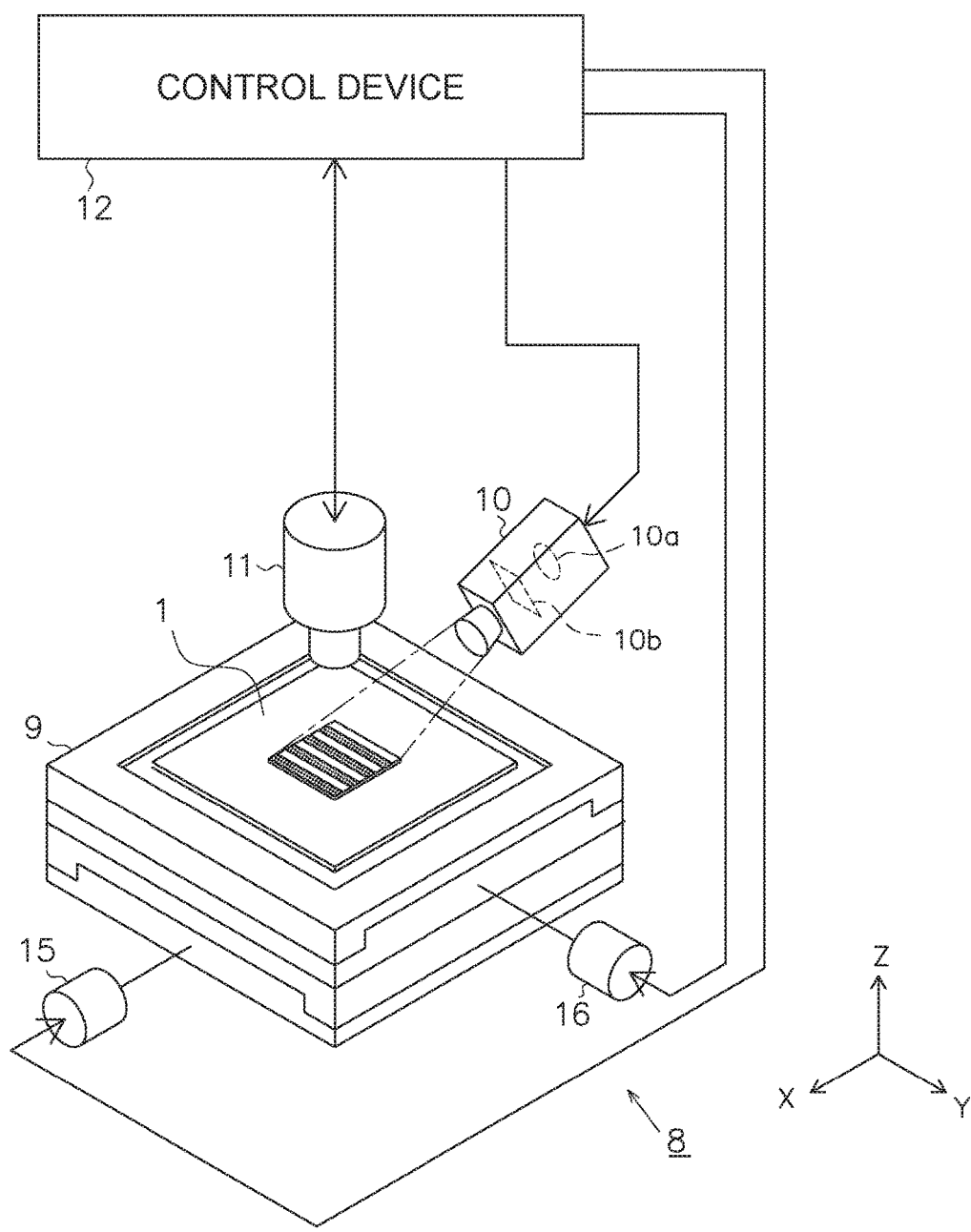
FIG. 1 is a schematic configuration diagram schematically illustrating a substrate inspection apparatus according to one or more embodiments of the invention.

The following describes a substrate inspection apparatus 8 equipped with a three-dimensional measurement device according to one or more embodiments of the invention in detail. FIG. 1 is a schematic configuration diagram schematically illustrating the substrate inspection apparatus 8. As illustrated in this diagram, the substrate inspection apparatus 8 includes a mounting table 9 configured to place the printed circuit board 1 thereon, an illumination device 10 as an irradiator configured to irradiate the surface of the printed circuit board 1 obliquely downward with a predetermined light pattern, a camera 11 as an imaging unit configured to take an image of an irradiated part that is irradiated with the light pattern on the printed circuit board 1 and a control device 12 configured to perform various controls image processing and calculations in the substrate inspection apparatus 8.

The mounting table 9 is provided with motors 15 and 16. The motors 15 and 16 are driven and controlled by the control device 12 to slide the printed circuit board 1 placed on the mounting table 9 in an arbitrary direction (X-axis direction and Y-axis direction).

The illumination device 10 includes a light source 10a and a liquid crystal grid 10b configured to convert light from the light source 10a into a light pattern having a sinusoidal (striped) light intensity distribution. The illumination device 10 is configured to radiate the striped light pattern having a phase changing in multiple different ways obliquely downward toward the printed circuit board 1.

For example, in the illumination device 10, the light emitted from the light source 10a is guided by an optical fiber into a pair of condenser lenses to be converted to parallel lights. The parallel lights are guided into a projection lens via the liquid crystal grid 10b. The striped light pattern is then radiated from the projection lens toward the printed circuit board 1.

The illumination device 10 is further configured to change the luminance of the light emitted from the light source 10a. According to one or more embodiments of the invention, a luminance setting process described later is performed to change over the luminance at least between a soldering luminance for the solder area and a background luminance for the background area. The "soldering luminance" corresponds to the "first luminance" according to one or more embodiments of the invention, and the "background luminance" corresponds to the "second luminance" according to one or more embodiments of the invention.

The liquid crystal grid 10b includes a liquid crystal layer that is formed between a pair of transparent substrates, a common electrode placed on one of the transparent substrate and a plurality of strip electrodes placed on the other transparent substrate to be opposed to the common electrode. A drive circuit controls on and off switching elements (for example, thin film transistors) respectively connected with the respective strip electrodes and regulates voltages that are to be applied to the respective strip electrodes, so as to change over the light transmittances of respective grid lines provided corresponding to the respective strip electrodes and thereby form a striped grid pattern including "bright portions" of the higher light transmittance and "dark portions" of the lower light transmittance. The light radiated onto the printed circuit board 1 via the liquid crystal grid 10b is a light pattern having a sinusoidal light intensity distribution, due to a blur or the like caused by diffraction effect.

The camera 11 is configured to include a lens, an imaging element and the like. A CMOS sensor is employed for the imaging element. The imaging element is, however, not limited to the CMOS sensor but may be, for example, a CCD sensor or the like. Image data taken by the camera 11 is converted into digital signals inside of the camera 11, is input in the form of digital signals into the control device 12 and is stored in a data storage device 24 described later. The control device 12 performs, for example, image processing and an inspection process as described later, based on the image data. From this point of view, the control device 12 is configured as the image processor.

Figure 3:
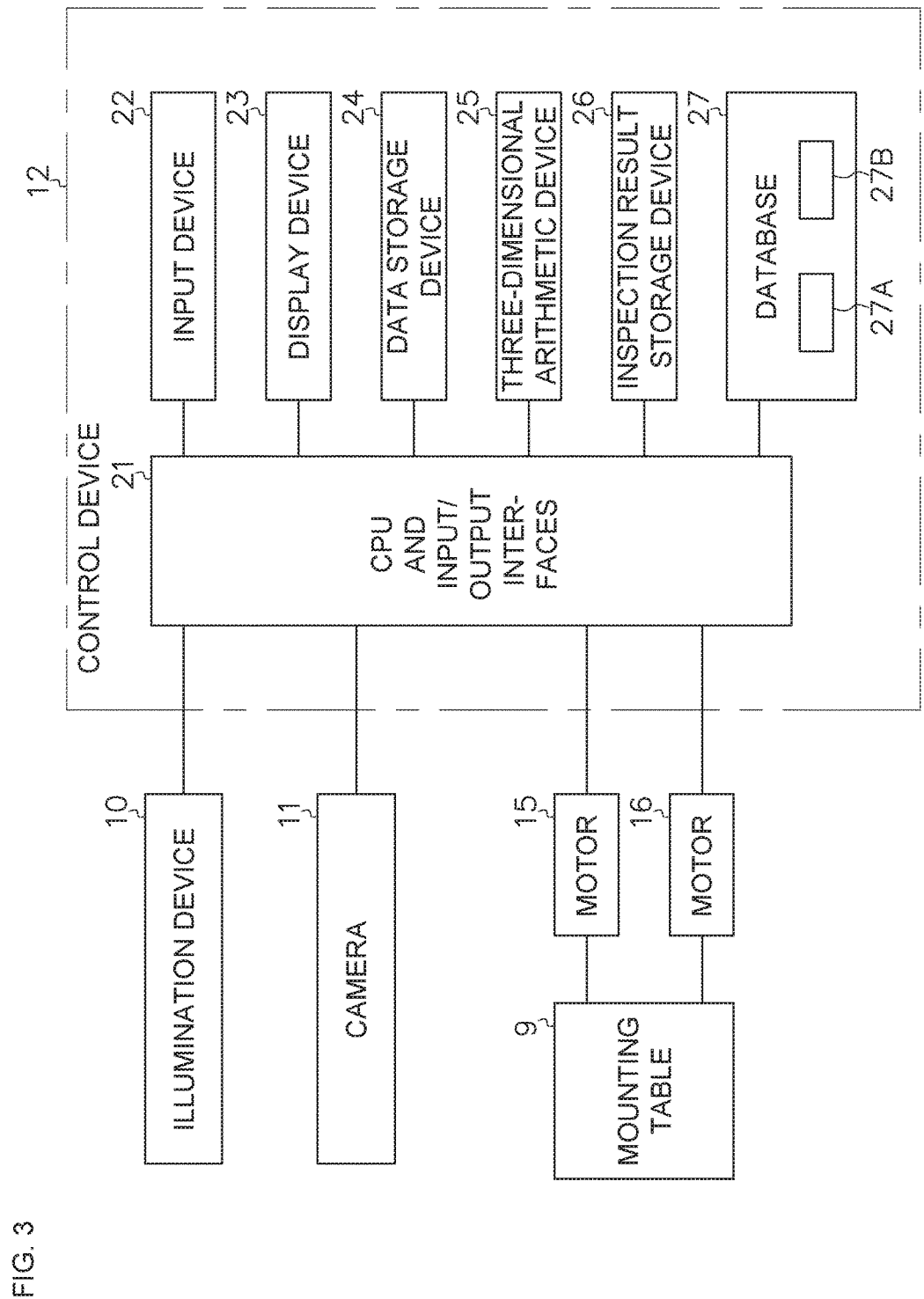
FIG. 3 is a block diagram illustrating the electrical configuration of the substrate inspection apparatus according to one or more embodiments of the invention.

The following describes the electrical configuration of the control device 12. As shown in FIG. 3, the control device 12 includes a CPU and input/output interfaces 21 (hereinafter referred to as "CPU and like 21") configured to control the entire substrate inspection apparatus 8, an input device 22 configured by a keyboard and a mouse or by a touch panel as the "input unit," a display device 23 configured as the "display unit" including a display screen such as a CRT or a liquid crystal screen, a data storage device 24 configured to store image data taken by the camera 11 and various calculation data, a three-dimensional arithmetic device 25 configured as the "three-dimensional arithmetic unit" to measure the height and the volume of the solder paste 4 or the like, an inspection result storage device 26 configured to store inspection results, and a database 27 configured to store various data required for inspection in advance. These devices 22 to 27 are electrically connected with the CPU and the like 21.

The database 27 stores a soldering table 27A showing a correspondence relationship between the solder area (type of the solder paste 4) and the luminance of the illumination device 10, and a substrate table 27B showing a correspondence relationship between the background area (type of the printed circuit board 1) and the luminance of the illumination device 10.

According to one or more embodiments of the invention, as shown in FIG. 4A, the soldering table 27A is configured to show a correspondence relationship between manufacturers of the solder paste 4 printed in the solder area, for example, a company, b company and c company, and values of the luminance of the illumination device 10. As shown in FIG. 4B, the substrate table 27B is configured to show a correspondence relationship between the colors of the background area, such as green, blue and black, and values of the luminance of the illumination device 10.

Figure 5:
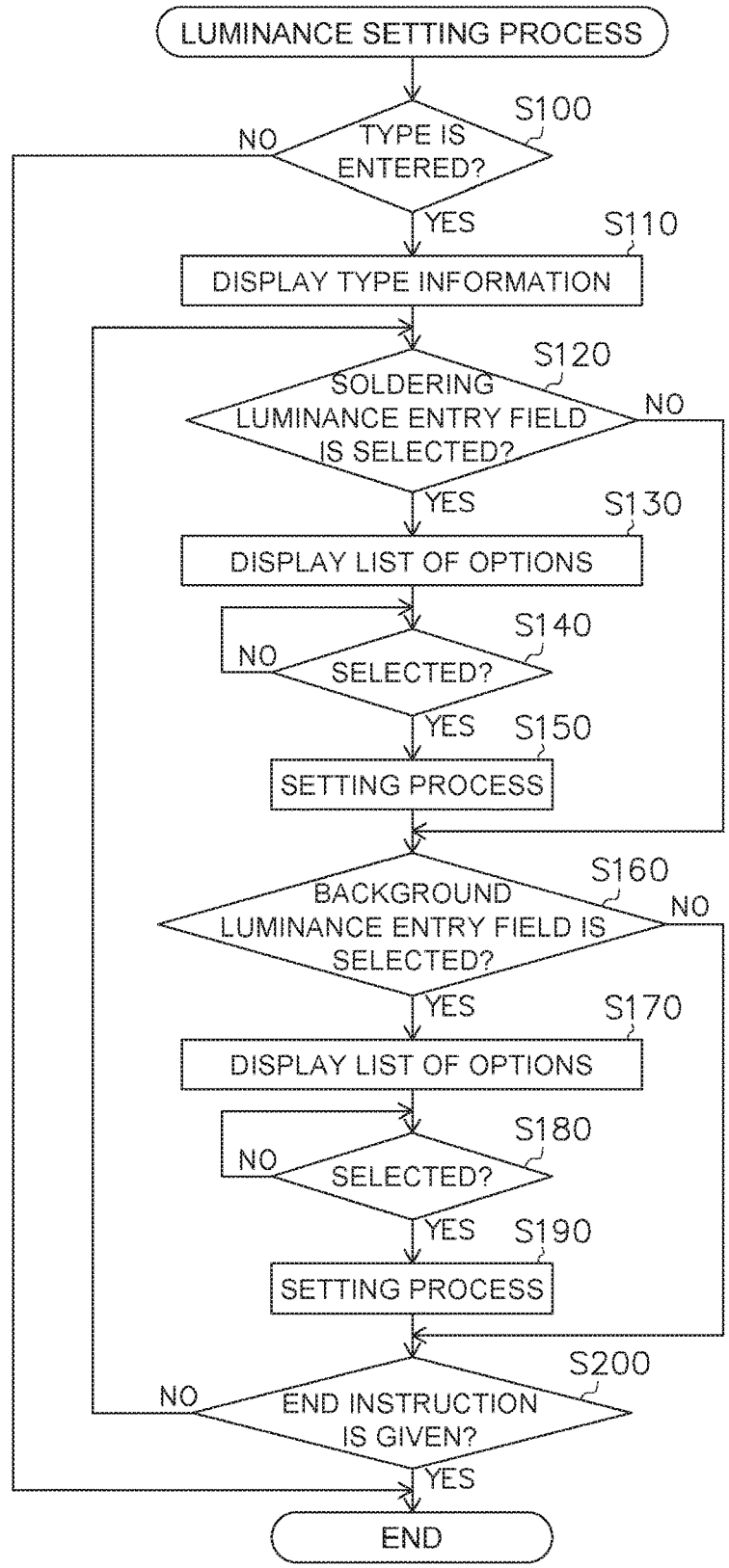
FIG. 5 is a flowchart showing a luminance setting process according to one or more embodiments of the invention.
Figure 6:
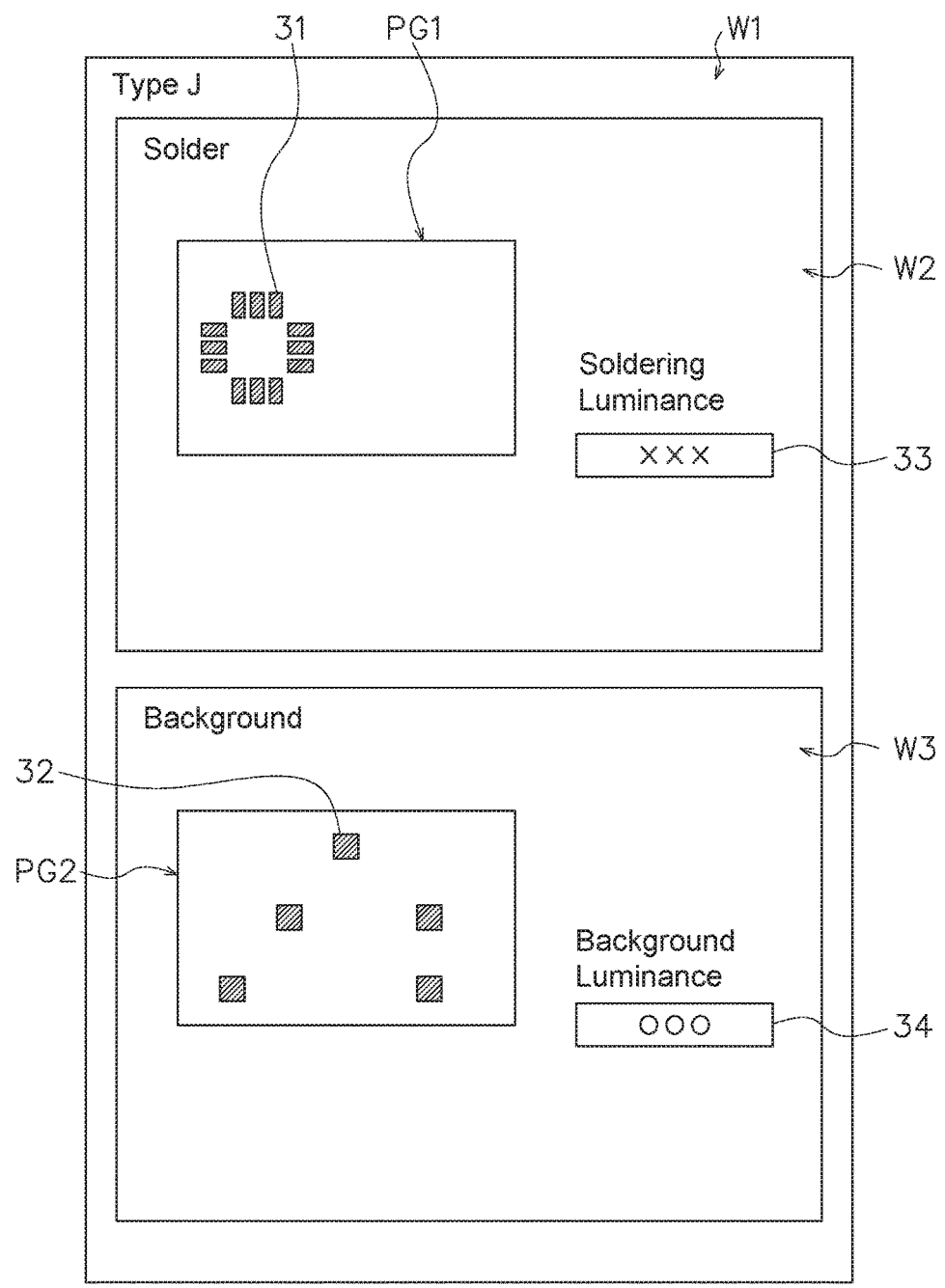
FIG. 6 is a diagram illustrating a display window of type information according to one or more embodiments of the invention.
Figure 7:
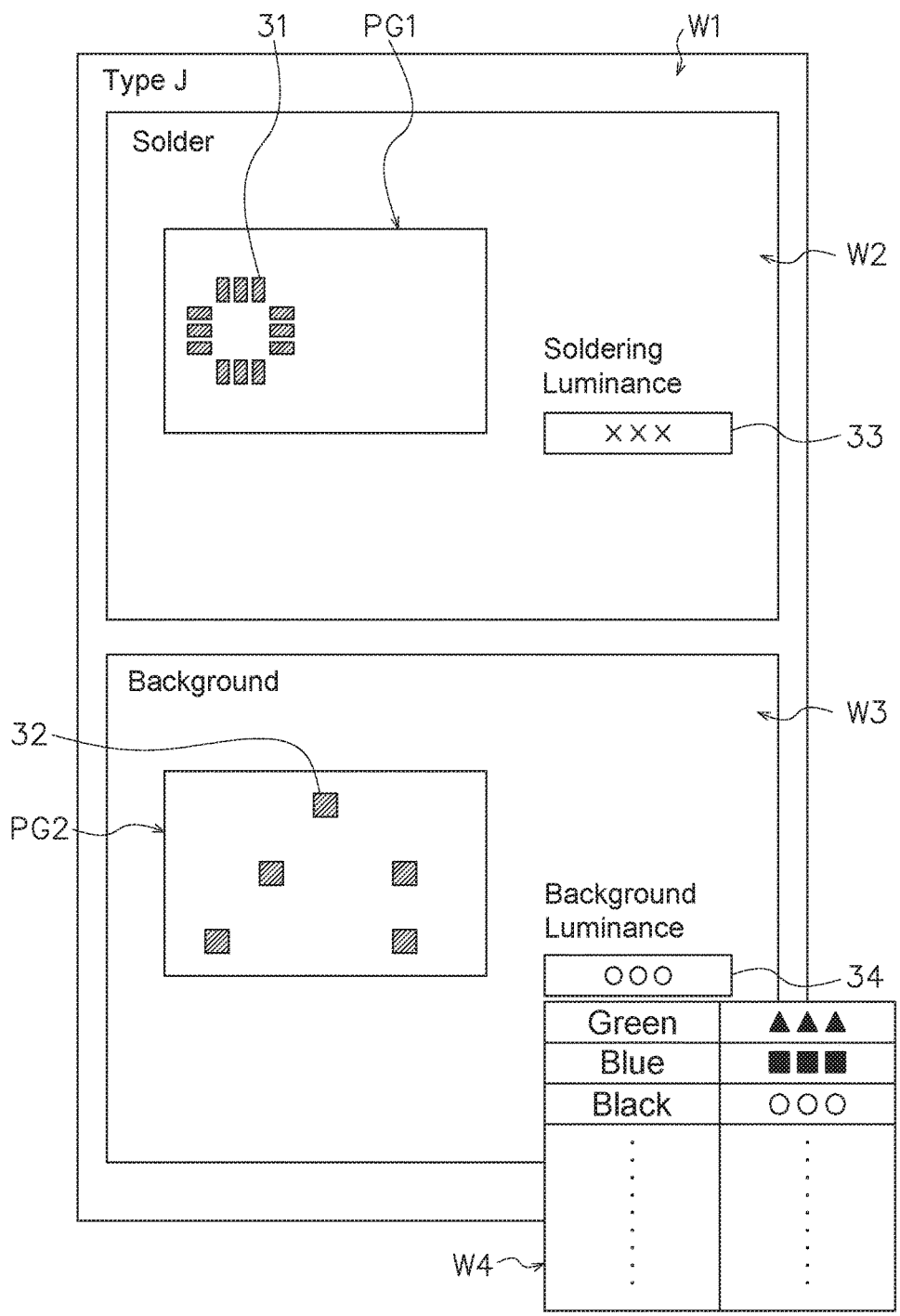
FIG. 7 is a diagram illustrating selection of a luminance in the display window of type information according to one or more embodiments of the invention.

The following describes a luminance setting process that is performed by the control device 12 to set the luminance of the illumination device 10, with reference to the flowchart of FIG. 5 and the diagrams of FIG. 6 and FIG. 7. This luminance setting process is repeatedly performed, in response to a selective operation of a "Set" button displayed on the display screen of the display device 23. The selective operation of the "Set" button is provided via the input device 22 and may be implemented, for example, by a configuration of selectively operating the "Set" button with a pointing device such as a mouse or by a configuration of selectively operating the "Set" button on a touch panel integrated with the display device 23.

At first step (hereinafter, step is simply represented by a reference sign S) 100, the control device 12 determines whether the type of the printed circuit board 1 as an inspection object is entered. An inspection area and the like with regard to the printed circuit board 1 are set in advance corresponding to each identified type of the printed circuit board 1. When it is determined that the type of the printed circuit board 1 is entered (S100: YES), the control device 12 displays type information at S110 and proceeds to S120. When it is determined that the type of the printed circuit board 1 is not entered (S100: NO), on the other hand, the control device 12 terminates this cycle of the luminance setting process without executing a subsequent series of process.

An example of display of the type information at S110 is shown in FIG. 6. This illustrated example shows the case where a "type J" is selected. For example, a window W1 is opened. This window W1 consists of windows W2 and W3. The window W2 shows information on the solder area, and the window W3 shows information on the background area. The windows W2 and W3 respectively include entire images PG1 and PG2 of the printed circuit board 1. The entire images PG1 and PG2 are provided in advance. The entire images PG1 and PG2 may otherwise be obtained, based on imaging by the camera 11.

The image PG1 for soldering displayed in the window W2 indicates inspection object areas 31 (areas filled with slant lines in the window W2) that are solder areas provided by printing the solder paste 4 and are specified as inspection objects. The "inspection object area" corresponds to the "first measurement object area" according to one or more embodiments of the invention.

The image PG2 for background displayed in the window W3, on the other hand, indicates measurement reference areas 32 (areas filled with slant lines in the window W3) that are part of the background area and are specified as a criterion of height measurement and the like. The "measurement reference area 32" corresponds to the "second measurement object area" according to one or more embodiments of the invention.

The window W2 also includes an entry field 33 for a soldering luminance, and the window W3 includes an entry field 34 for a background luminance. Default luminance values may be shown in these entry fields 33 and 34, or the entry fields 33 and 34 may be provided as vacant fields in the stage of S110.

Referring back to FIG. 5, the control device 12 determines whether the entry filed 33 for the soldering luminance is selected at S120. Selection of the entry field 33 for the soldering luminance is implemented by a selective operation via the input device 22. For example, like the selective operation of the "Set" button described above, selection of the entry field 33 may be implemented, for example, by a configuration of selectively operating the entry field 33 with a pointing device such as a mouse or by a configuration of selectively operating the entry field 33 on a touch panel integrated with the display device 23. The same applies to selective operations on the display screen in the subsequent description. When it is determined that the entry field 33 is selected (S120: YES), the control device 12 displays a list of options (described later) at S130 and proceeds to S140. When it is determined that the entry field 33 is not selected (S120: NO), on the other hand, the control device 12 proceeds to S160.

The control device 12 determines whether a luminance value is selected from the list of options at S140. When it is determined that a luminance value is selected (S140: YES), the control device 12 performs a process of setting the soldering luminance at S150 and proceeds to S160. When it is determined that no luminance value is selected (S140: NO), on the other hand, the control device 12 repeats this determination process. When no luminance value has been selected even after elapse of a predetermined time period, the process may be terminated or an alarm or the like may be given (the same applies to S180).

The control device 12 determines whether the entry field 34 for the background luminance is selected at S160. Selection of the entry field 34 for the background luminance is implemented by a selective operation via the input device 22. When it is determined that the entry field 34 is selected (S160: YES), the control device 12 displays a list of options described later at S170 and proceeds to S180. When it is determined that the entry field 34 is not selected (S160: NO), on the other hand, the control device 12 proceeds to S200.

The control device 12 determines whether a luminance value is selected from the list of options at S180. When it is determined that a luminance value is selected (S180: YES), the control device 12 performs a process of setting the background luminance at S190 and proceeds to S200. As long as no luminance value is selected (S180: NO), on the other hand, the control device 12 repeats this determination process.

The control device 12 determines whether an end instruction is given at S200. This end instruction is given by a selective operation of an "End" button on the non-illustrated screen. When it is determined that an end instruction is given (S200: YES), the control device 12 terminates this luminance setting process. When it is determined that no end instruction is given (S200: NO), on the other hand, the control device 12 repeats the series of process of and after S120.

The following describes the above selection and setting of the luminance value (S120 to S190) with reference to a concrete example. The following description regards the selection and setting of the background luminance (S160 to S190). The same applies to the selection and setting of the soldering luminance (S120 to S150).

The following description is on the assumption that the information on the type J of the printed circuit board 1 is displayed as shown in FIG. 6. The list of options at S170 may be displayed in a configuration shown in FIG. 7. For example, when the entry field 34 for the background luminance is selected (S160: YES), a new window W4 is opened below the entry field 34. The content of the displayed list of options shows the correspondence relationship between the color and the luminance in the substrate table shown in FIG. 4B. When a luminance value (for example, shown by closed triangles in the diagram) in this list of options is selected (S180: YES), the selected luminance value is set (S190) and is shown in the entry field 34 for the background luminance. The luminance value is selected at S180. According to a modification, however, a substrate type (color) such as "green," "blue" or "black" may be selected, or either one of the luminance value and the substrate type may be selected.

On completion of setting the soldering luminance and the background luminance, inspection of the printed circuit board 1 is ready for start.

The following describes a procedure of inspection of the printed circuit board 1 by the substrate inspection apparatus 8, based on an inspection routine performed for each inspection area. This inspection routine is performed by the control device 12 (CPU and the like 21).

The control device 12 first drives and controls the motors 15 and 16 to move the printed circuit board 1 and adjust the field of view of the camera 11 to a predetermined inspection area (measurement range) on the printed circuit board 1. The inspection area denotes one of divisional areas provided by dividing the surface of the printed circuit board 1 in advance with setting the size of the field of view of the camera 11 as one unit.

The control device 12 subsequently performs a setting process of the illumination device 10. For example, the control device 12 performs a changeover control process of the luminance of the light source 10a and a changeover control process of the liquid crystal grid 10b. Concretely, the luminance of the light emitted from the light source 10a is changed over and set equal to the soldering luminance (first luminance) determined in advance by the luminance setting process described above, and the changeover control of the liquid crystal grid 10b sets the position of a grid formed in the liquid crystal grid 10b to a predetermined reference position (having the phase of "0 degree"). The function of the control device 12 to perform the changeover control process of the luminance of the light source 10a is configured as the "luminance controller" according to one or more embodiments of the invention, and the function of the control device 12 to perform the changeover control process of the liquid crystal grid 10b is configured as the "phase controller" according to one or more embodiments of the invention.

On completion of the changeover setting of the light source 10a and the liquid crystal grid 10b, the control device 12 controls the light source 10a of the illumination device 10 to start emission of a first light pattern for the soldering luminance and sequentially shifts the phase of the first light pattern by 90 degrees each in four different phase levels (phase of "0 degree," phase of "90 degrees," phase of "180 degrees" and phase of "270 degrees").

Every time the phase of the first light pattern is sequentially shifted, the control device 12 drives and controls the camera 11 to take an image of an inspection area portion irradiated with the first light pattern. Accordingly, four different image data taken under the first light pattern with the phase shifted by 90 degrees each are obtained with regard to the predetermined inspection area. The image data taken by the camera 11 are transferred to the data storage device 24 and are stored therein.

The control device 12 (three-dimensional arithmetic device 25) subsequently calculates a phase $\theta_1$ of the first light pattern with regard to each pixel from the above four different image data (luminance values) by the phase shift method.

Luminance values $V_{10}$, $V_{11}$, $V_{12}$ and $V_{13}$ of the above four different image data with regard to each pixel are expressed by Expressions (H1), (H2), (H3) and (H4) given below:

[Math. 11]

$$V_{10}=A_1 \sin\theta_1 + B_1 \tag{H1}$$

$$V_{11}=A_1 \sin(\theta_1+90°)+B_1=A\cos\theta_1+B_1 \tag{H2}$$

$$V_{12}=A_1 \sin(\theta_1+180°)+B_1=-A\cos\theta_1+B_1 \tag{H3}$$

$$V_{13}=A_1 \sin(\theta_1+270°)+B_1=-A\cos\theta_1+B_1 \tag{H4}$$

$A_1$ denotes a gain of the first light pattern, and $B_1$ denotes an offset of the first light pattern.

Expression (H5) given below is derived by solving Expressions (H1), (H2), (H3) and (H4) given above with respect to the phase $\theta_1$:

[Math. 12]

$$\theta_1 = \tan^{-1}\{(V_{10}-V_{12})/(V_{11}-V_{13})\} \tag{H5}$$

The control device 12 subsequently calculates height data (z) with regard to each pixel (x,y) in the inspection object area 31 using the phase $\theta_1$ calculated as described above, based on the principle of triangulation, and stores the calculated height data (z) into the inspection result storage device 26. This series of process function is configured as the first measurement unit according to one or more embodiments of the invention.

The control device 12 then grasps a relationship between a gain $A_1$ and an offset $B_1$ with regard to each pixel from the above four different image data taken under the first light pattern and stores the grasped relationship into the data storage device 24. This process function is configured as the relationship grasping unit according to one or more embodiments of the invention. The process of grasping the relationship between the gain $A_1$ and the offset $B_1$ is performed in parallel with the process of calculating the height data with regard to the inspection object area 31, after the four different image, data are obtained (after imaging).

A procedure of grasping the relationship between the gain $A_1$ and the offset $B_1$ or a procedure of calculating a proportional constant K of the gain $A_1$ and the offset $B_1$ is described more in detail. Expressions (H1) to (H4) given above show relationships of the gain $A_1$ and the offset $B_1$ to the luminance values $V_{10}$, $V_{11}$, $V_{12}$ and $V_{13}$ of the four different image data with regard to each pixel.

Expression (H6) given below is derived by summing up the luminance values $V_{10}$, $V_{11}$, $V_{12}$ and $V_{13}$ of the four different image data and reorganizing Expressions (H1) to (H4) given above as shown in [Math. 13] given below:

[Math. 13]

$$V_{10}+V_{11}+V_{12}+V_{13} = (A_1\sin\theta_1+B_1)+(A_1\cos\theta_1+B_1)+ \tag{H6}$$
$$(-A_1\sin\theta_1+B_1)+(-A_1\cos\theta_1+B_1)$$
$$= 4B_1$$

$$B_1 = (V_{10}+V_{11}+V_{12}+V_{13})/4$$

Expression (H7) given below is derived from Expressions (H1) and (H3) given above:

[Math. 14]

from $V_{10}-V_{12}=2A_1 \sin\theta_1$, $$\sin\theta_1=(V_{10}-V_{12})/2A_1 \tag{H7}$$

Expression (H8) given below is derived from Expressions (H2) and (H4) given above:

[Math. 15]

from $V_{11}-V_{13}=2A_1 \cos\theta_1$, $$\cos\theta_1=(V_{11}-V_{13})/2A_1 \tag{H8}$$

Expression (H10) given below is derived by substituting Expressions (H7) and (H8) given above into Expression (H9) given below and reorganizing these expressions as shown in [Math. 16] given below:

[Math. 16]

$$1 = \sin^2\theta_1 + \cos^2\theta_1 \tag{H9}$$

$$1 = \{(V_{10}-V_{12})/2A_1\}^2 + \{(V_{11}-V_{13})/2A_1\}^2 \tag{H10}$$

$$4A_1^2 = (V_{10}-V_{12})^2 + (V_{11}-V_{13})^2$$

$$A_1 = \sqrt{\frac{(V_{10}-V_{12})^2+(V_{11}-V_{13})^2}{4}}$$

where $A_1 > 0$

The proportional constant K of the gain $A_1$ and the offset $B_1$ is calculated according to Expression (H11) given below as being derived from Expressions (H6) and (H10) given above:

[Math. 17]

$$K = A_1/B_1 \tag{H11}$$

$$= \frac{\sqrt{\frac{(V_{10}-V_{12})^2+(V_{11}-V_{13})^2}{4}}}{\frac{V_{10}+V_{11}+V_{12}+V_{13}}{4}}$$

$$= 2\times\frac{\sqrt{(V_{10}-V_{12})^2+(V_{11}-V_{13})^2}}{V_{10}+V_{11}+V_{12}+V_{13}}$$

The proportional constant K of the gain $A_1$ and the offset $B_1$ calculated as described above with regard to each pixel is stored in the data storage device 24.

The control device 12 subsequently starts an imaging process with regard to the measurement reference area 32. The imaging process with regard to the measurement reference area 32 is started immediately after completion of the series of imaging process with regard to the inspection object area 31. Accordingly, the imaging process with regard to the measurement reference area 32 is performed in parallel with the process of calculating the height data with regard to the inspection object area 31 and the process of calculating the proportional constant K of the gain $A_1$ and e offset $B_1$ described above.

For example, the control device 12 performs the changeover control process of the luminance of the light source 10a and the changeover control process of the liquid crystal grid 10b. Concretely, the luminance of the light emitted from the light source 10a is changed over and set equal to the background luminance (second luminance) determined in advance by the luminance setting process described above, and the changeover control of the liquid crystal grid 10b sets the position of a grid formed in the liquid crystal grid 10b to a predetermined reference position (having the phase of "0 degree").

On completion of the changeover setting of the light source 10*a* and the liquid crystal grid 10*b*, the control device 12 controls the light source 10*a* of the illumination device 10 to start emission of a second light pattern for the background luminance and sequentially shifts the phase of the second light pattern in two different phase levels (phase of "0 degree" and phase of "180 degrees").

Every time the phase of the second light pattern is sequentially shifted, the control device 12 drives and controls the camera 11 to take an image of an inspection area portion irradiated with the second light pattern. Accordingly, two different image data taken under the second light pattern with the phase shifted by 180 degrees are obtained with regard to the predetermined inspection area. The image data taken by the camera 11 are transferred to the data storage device 24 and are stored therein.

The control device 12 subsequently calculates a phase $\theta_2$ of the second light pattern with regard to each pixel in the measurement reference area 32 from the above two different image data by the phase shift method.

Concretely, the phase $\theta_2$ of the second light pattern is expressed by Equation (15') given below, based on Equation (15) given above, when $V_{20}$ and $V_{21}$ respectively denote luminance values of the above two different image data with regard to each pixel:

$$\theta_2 = \sin^{-1}\left[(V_{20} - V_{21})/K(V_{20} + V_{21})\right] \quad (15')$$

where K denotes a proportional constant.

According to one or more embodiments of the invention, a relationship between a gain $A_2$ and an offset $B_2$ (proportional constant $K = A_2/B_2$) with regard to each pixel in the above two different image data taken under the second light pattern is equal to the relationship between the gain $A_1$ and the offset $B_1$ (proportional constant $K = A_1/B_1$) with regard to each pixel in the above four different image data taken under the first light pattern. A known value stored in the data storage device 24 is accordingly used as the proportional constant K (as shown in Expression (H11) given above).

The control device 12 subsequently calculates height data (z) with regard to each pixel (x,y) in the measurement reference area 32 using the phase $\theta_2$ calculated as described above, based on the principle of triangulation, and stores the calculated height data (z) into the inspection result storage device 26. This series of process function is configured as the second measurement unit according to one or more embodiments of the invention.

The control device 12 subsequently calculates the height, the volume, the printing range, and the like of the solder paste 4 in the inspection object area 31 relative to the measurement reference area 32 as the height reference surface. The control device 12 then compares the data such as the position, the area, the height or the volume of the solder paste 4 thus calculated with reference data stored in advance and determines the good/poor quality of the printing state of the solder paste 4 in the inspection area, based on whether the result of the comparison is within an allowable range. This inspection result is stored in the inspection result storage device 26.

During this process, the control device 12 drives and controls the motors 15 and 16 to move the printed circuit board 1 and set a next inspection area. The above series of process is then repeatedly performed with regard to all the inspection areas, so that inspection of the entire printed circuit board 1 is completed.

As described above in detail, one or more embodiments of the invention are configured to perform three-dimensional measurement of the inspection object area 31, based on image data taken by radiating the first light pattern of the first luminance corresponding to the inspection object area 31 and to perform three-dimensional measurement of the measurement reference area 32, based on image data taken by radiating the second light pattern of the second luminance corresponding to the measurement reference area 32. This configuration changes the luminance levels for the inspection object area 31 and the measurement reference area 32 and allows for three-dimensional measurement, based on image data taken under the light patterns of respectively adequate luminance levels. As a result, this suppresses a decrease in the measurement accuracy.

Additionally, one or more embodiments of the invention are configured to grasp the relationship between the gain A and the offset B (proportional constant K) of the light pattern determined according to the predetermined imaging condition, from the four different image data taken for the purpose of measurement of the inspection object area 31 and to perform three-dimensional measurement of the measurement reference area 32 by the phase shift method, based on the two different image data taken under the light pattern having the two different phase changes by using the grasped relationship between the gain A and the offset B of this light pattern and the values of the gain A and the offset B of the light pattern with respect to each pixel determined according to the luminance value V of each pixel on the image data.

Accordingly, one or more embodiments of the invention are configured to take four different image data by radiating the first light pattern of the first luminance in four different phases and to take two different image data by radiating the second light pattern of the second luminance in two different phases. The required number of imaging operations is thus a total of six times. This significantly decreases the imaging time.

Accordingly, one or more embodiments of the invention reduce the total number of imaging operations and shorten the imaging time. As a result, this remarkably shortens the measurement time.

One or more embodiments of the invention are configured to perform three-dimensional measurement of the measurement reference area 32, based on two different image data having different phases by 180 degrees. This provides a relatively narrow measurement range of 180 degrees, i.e., from −90 degrees to 90 degrees. The measurement reference area 32 as the reference surface is, however, flat and has an approximately uniform height. The narrow measurement range accordingly does not affect the effects of the embodiments of the invention.

Moreover, according to one or more embodiments of the invention, the luminance corresponding to the substrate type (substrate color) of "black" is provided in the substrate table 27B shown in FIG. 4B. When the measurement reference area 32 (background area) is in black or in gray relatively close to black, image data taken with the luminance corresponding to the inspection object area 31 is more likely to have a small difference between light and dark (luminance difference) in the measurement reference area 32. The configuration of the embodiments accordingly has prominent advantageous effects when the measurement reference area 32 is in black or in gray relatively close to black.

The following describes further embodiments of the invention with reference to drawings. The like components to those of the aforementioned embodiments are expressed by the like reference signs, and their detailed description is omitted. The different parts from the aforementioned embodiments are described mainly below.

One or more embodiments of the inventor figured to determine whether three-dimensional measurement of the measurement reference area 32 is possible or impossible, based on image data taken by radiating the light pattern of the first luminance corresponding to the inspection object area 31, and to correct the first luminance to the second luminance corresponding to the measurement reference area 32 and radiate the light pattern of the second luminance when it is determined that three-dimensional measurement is impossible.

Figure 8:
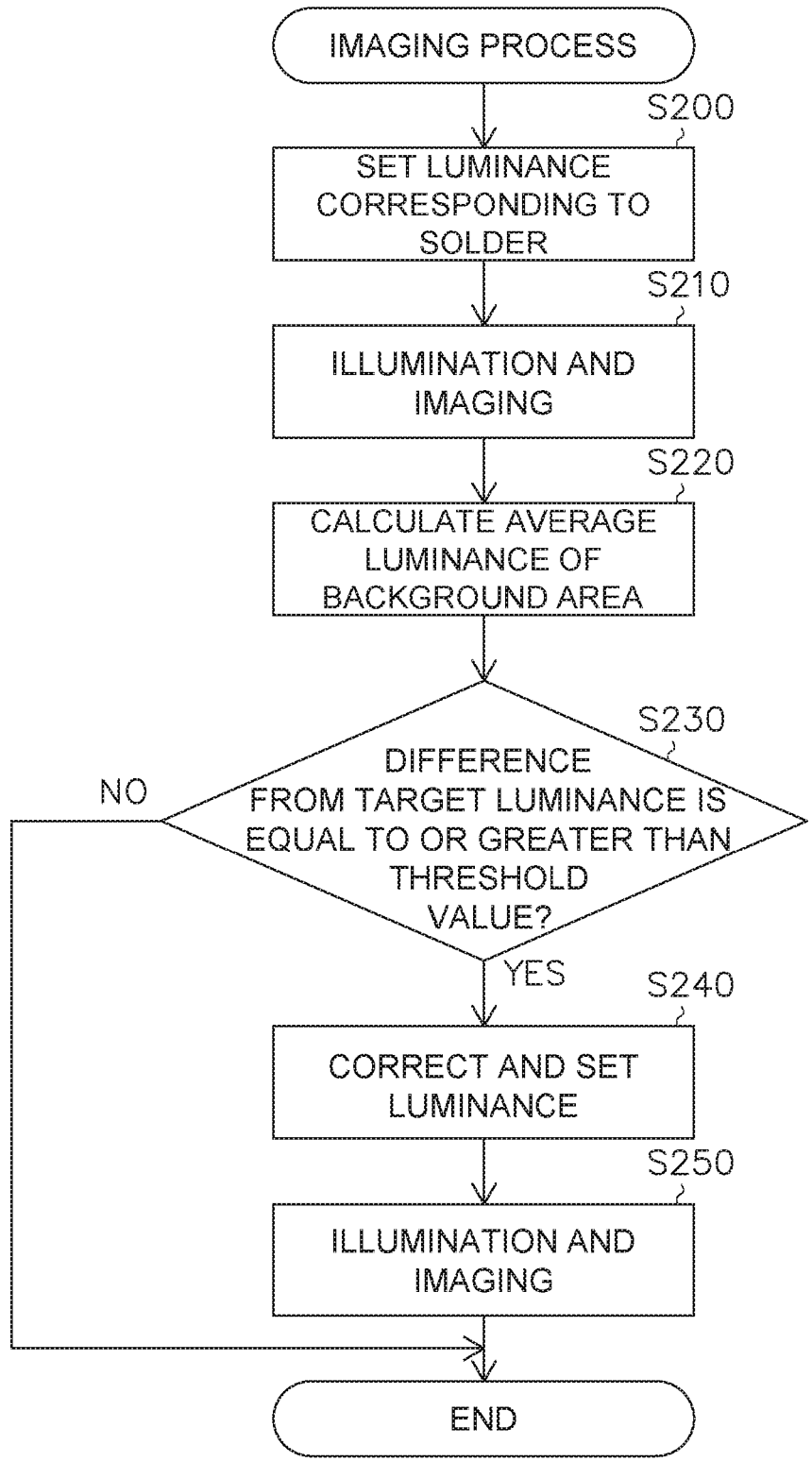
FIG. 8 is a flowchart showing an imaging process according to one or more embodiments of the invention.

The following describes in detail a series of imaging process with regard to measurement of the inspection object area 31 and the measurement reference area 32 with reference the flowchart of FIG. 8.

At first step (hereinafter, step is simply represented by a reference sign S) 200, the control device 12 sets the luminance of the illumination device 10 according to the solder paste 4. This luminance determined in advance as the soldering luminance (first luminance).

At subsequent S210, the control device 12 lights up the illumination device 10 to have the set soldering luminance and irradiates the surface of the printed circuit board 1 obliquely downward with the first light pattern of the first luminance. Every time the phase of the first light pattern is sequentially shifted, the control device 12 drives and controls the camera 11 to take an image of an inspection area portion irradiated with the first light pattern. This provides four different image data taken under the first light pattern having the phase shifted by 90 degrees each.

At subsequent S220, the control device 12 calculates an average luminance of the background area, based on the image data taken at S210.

At subsequent S230, the control device 12 determines whether a difference between a target luminance of the background area and the average luminance calculated at S220 is equal to or greater than a threshold value. When it is determined that the difference is equal to or greater than the threshold value (S230: YES), the control device 12 proceeds to S240. When the difference is smaller than the threshold value (S230: NO), on the other hand, the control device 12 terminates this imaging process without executing a subsequent series of process.

The control device 12 corrects the luminance at S240 when it is determined that the difference is equal to or greater than the threshold value. For example, the luminance of the illumination device 10 is corrected and set, based on a ratio of the average luminance calculated at S220 to the target luminance. Accordingly, this corrects the soldering luminance (first luminance) and sets the background luminance (second luminance).

At S250, the control device 12 lights up the illumination device 10 to have the corrected background luminance and irradiates the surface of the printed circuit board 1 obliquely downward with the second light pattern of the second luminance. Every time the phase of the second light pattern is sequentially shifted, the control device 12 drives and controls the camera 11 to take an image of an inspection area portion irradiated with the second light pattern. This provides two different image data taken under the second light pattern having the phase shifted by 180 degrees.

A concrete example is described below, in order to facilitate understanding of the above imaging process.

Figure 9:
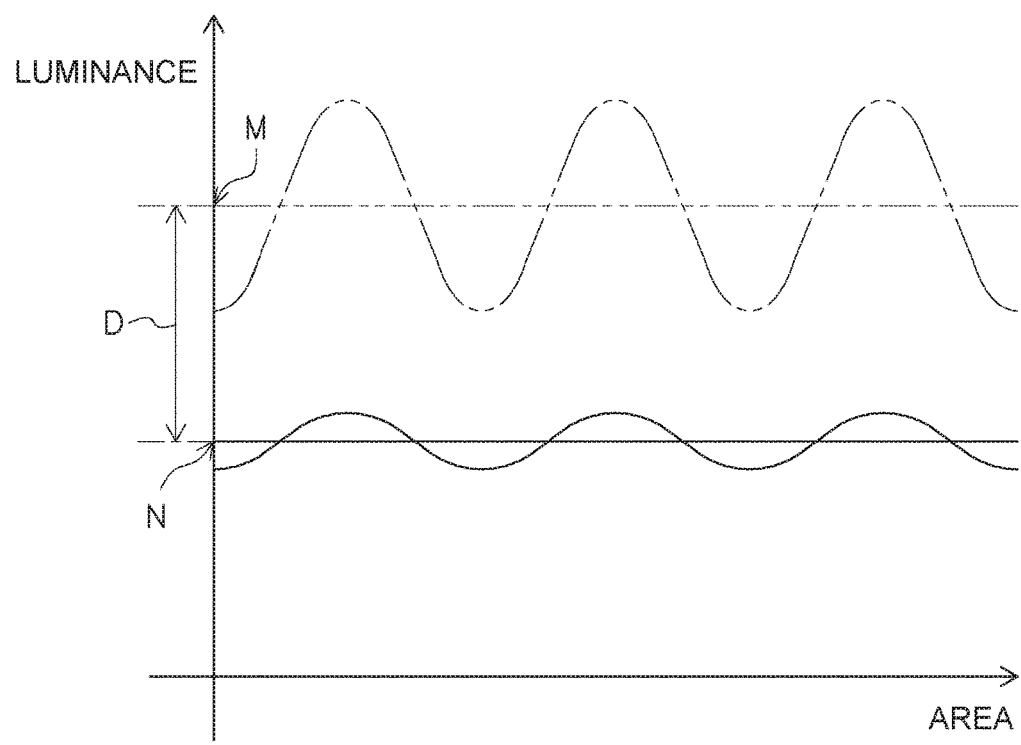
FIG. 9 is a diagram illustrating correction of the luminance according to one or more embodiments of the invention.

FIG. 9 is a graph schematically illustrating a variation in luminance of the light pattern in the background area. An ideal variation in luminance for three-dimensional measurement of the background area (measurement reference area 32) is shown by a two-dot chain line curve on the upper part of the graph. In the case of radiation of the striped light pattern, the luminance variation curve is a sine curve having a certain amplitude. When the background area is in a relatively dark color, however, imaging with the luminance corresponding to the solder area (inspection object area 31) is likely to give a sine curve of a small amplitude as shown by a solid line curve on the lower part of the graph. This provides a small difference between light and dark (luminance difference).

In the above imaging process, the control device 12 calculates the average luminance of the background area (S220 in FIG. 8), determines whether the difference between the calculated average luminance and the target luminance is equal to or greater than the threshold value (S230), and corrects the soldering luminance and sets the background luminance (S240) when the difference is equal to or greater than the threshold value (S230: YES). With reference to the example of FIG. 9, the control device 12 calculates the average value of the luminance of the background area, i.e., an average value N of the sine curve on the lower part of the graph (S220) and determines whether a difference D between the calculated average value N and a target value M that is an average value of ideal luminance determined in advance is equal to or greater than the threshold value (S230). When the difference D is equal to or greater than the threshold value (S230: YES), the control device 12 corrects the soldering luminance and sets the background luminance, based on a ratio of the average value N to the target value M. For example, the background luminance is set by multiplying the soldering luminance by (M/N)-fold.

The control device 12 then performs three-dimensional measurement of the measurement reference area 32 based on the image data obtained by radiation with the background luminance, and performs three-dimensional measurement of the inspection object area 31 based on the image data obtained by radiation with the soldering luminance.

When illumination or imaging is not performed with the background luminance, on the other hand, the control device 12 performs three-dimensional measurement of the inspection object area 31 and the measurement reference area 32, based on image data obtained by radiation with the soldering luminance.

The control device 12 then measures the height and the volume of the solder paste 4 in the inspection object area 31 relative to the measurement reference area 32 as the height reference surface.

As described above in detail, the further embodiments of the invention have similar functions and advantageous effects to those of the aforementioned embodiments described above.

Additionally, according to one or more embodiments of the invention, the control device 12 lights up the illumination device 10 with the soldering luminance that is determined in advance corresponding to the solder area (inspection object area 31) and performs imaging (S200 and S210 in FIG. 8), on the assumption that the color of the solder paste 4 does not significantly differ among manufacturers. The control device 12 performs three-dimensional measurement of the inspection object area 31, based on the image data taken under the first light pattern of this soldering luminance. The control device 12 subsequently calculates the average value of the luminance in the background area, based on the image data taken under this first light pattern (S220), and corrects the soldering luminance and sets the background luminance using the ratio of the average value to the target value (S240) when the difference between the calculated average value and the target value of luminance is equal to or greater than the threshold value (S230: YES). After setting the background luminance, the control device 12 lights up the illumination device 10 with this background luminance and performs imaging (S250). This allows for three-dimensional measurement of the measurement reference area 32, based on the image data taken under the second light pattern of this background luminance.

As described above, when the measurement reference area 32 (background area) is in black or in gray relatively close to black, the image data taken with the luminance corresponding to the inspection object area 31 is more likely to have a small difference between light and dark (luminance difference) in the background area. In this case, the configuration of one or more embodiments of the invention allows for three-dimensional measurement of the measurement reference area 32 with correcting the luminance with the ratio of the average value of the actual luminance to the target value. This gives prominent advantageous effects when e measurement reference area 32 is in black or in gray relatively close to black.

The present disclosure is not limited to the description of the above embodiments but may be implemented, for example, by configurations described below. The present disclosure may also be naturally implemented by applications and modifications other than those illustrated below.

(a) According to the above embodiment, the three-dimensional measurement device is embodied in the substrate inspection apparatus 8 configured to measure the height or the like of the solder paste 4 printed and formed the printed circuit board 1. This is, however, not restrictive. For example, the three-dimensional measurement device may be embodied in a configuration of measuring the height of another object, for example, a solder bump printed on a substrate or an electronic component mounted on a substrate. For example, in the case of a wafer substrate, the surface of an oxide film may be used as a reference height, and the height, the shape, the volume and the like of the solder bump may be calculated.

(b) The above embodiment employs the liquid crystal grid 10b for the grid configured to convert the light from the light source 10a into a striped light pattern and is configured to shift the phase of the light pattern by changeover control of the liquid crystal grid 10b. This configuration is, however, not restrictive. For example, a modification may be configured to move a grid member by a moving unit such as a piezoelectric actuator, so as to shift the phase of the light pattern.

(c) The above embodiment is configured to perform three-dimensional measurement of the first measurement object area (inspection object area 31) with the first light pattern by the phase shift method, based on the four different image data taken under the first light pattern having the four different phases that differ by 90 degrees each. This configuration is, however, not restrictive. For example, a modification may be configured to perform three-dimensional measurement, based on three different image data taken under the first light pattern having three different phases that differ by 120 degrees each. Accordingly, the "predetermined number" that is the number of imaging operations in the first measurement object area under the first light pattern ay be any number that allows for at least three-dimensional measurement by the phase shift method.

(d) The above embodiment is configured to perform three-dimensional measurement of the second measurement object area (measurement reference area 32) with the second light patty based on the two different image data taken under the second light pattern having the two different phases that differ by 180 degrees. This configuration may be replaced by, for example, a modification configured to perform three-dimensional measurement, based on two different image data taken under a light pattern having two different phases that differ by 90 degrees. In this modification, the phase $\theta_2$ of the second light pattern in each pixel may be calculated from the luminance values $V_{20}$ and $V_{21}$ in each pixel of the two different image data and the known proportional constant K according to Expressions (23) and (27) given above.

This modified configuration determines the phase $\theta_2$ according to the arithmetic expression using "$\tan^{-1}$," This allows for measurement of the height in the range of 360 degrees from −180 degrees to 180 degrees and further expands the measurement range.

Any other configuration that satisfies the relations of Expressions (1), (2) and (3) given above may also be employed. An example of the general expression to obtain the phase $\theta_2$ is Expression (9) given above (as shown in [Math. 9]).

(e) The configuration of the relationship grasping unit to grasp the relationship between the gain A and the offset B is not limited to the above embodiment.

For example, the relationship between the gain A and the offset B may not be specified as an expression but may be configured such that the offset B is determinable according to the gain A or the gain A is determinable according to the offset B by referring to a numerical table or table data provided to indicate the relationship between the gain A and the offset B.

(f) The embodiments described above are configured to store the soldering table 27A including luminance values that differ among the manufacturers. When the color of the solder area. (area in which the solder paste 4 is printed) is relatively stable, the soldering table 27A may be omitted. In other words, like the further embodiments discussed above, the illumination device 10 may be lit up with a predetermined luminance in imaging for the purpose of measurement of the inspection object area 31 by taking into account the fact that the color of the solder paste does not significantly differ among the manufacturers.

(g) The above embodiment is configured to set an identical background luminance for a plurality of measurement reference areas 32 (background areas) and to perform imaging by radiation of the illumination device 10 with this background luminance.

Figure 10:
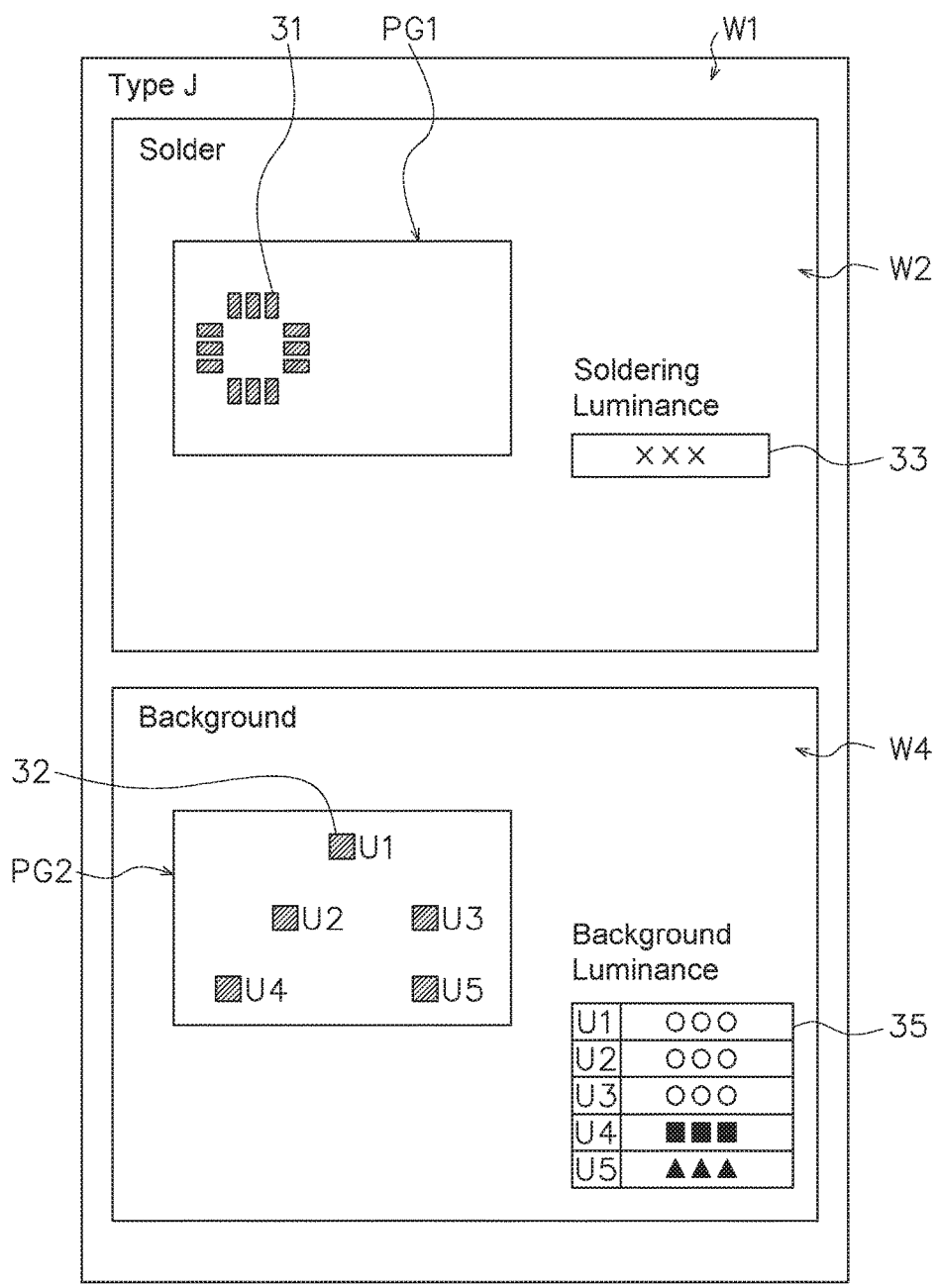
FIG. 10 is a diagram illustrating a display window of type information according to one or more embodiments of the invention.
Figure 11:
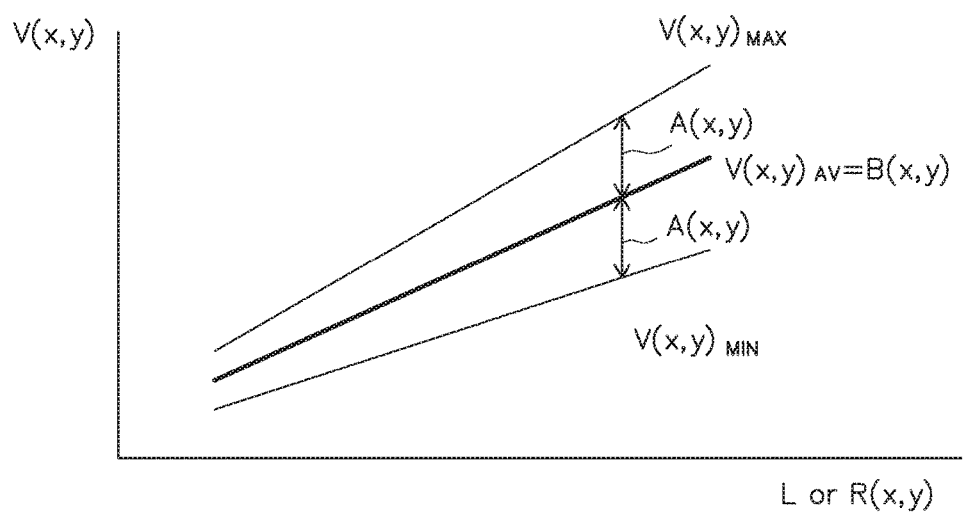
FIG. 11 is a graph showing a relationship between a luminance or reflectance of a light source and a luminance value according to one or more embodiments of the invention.
Figure 12:
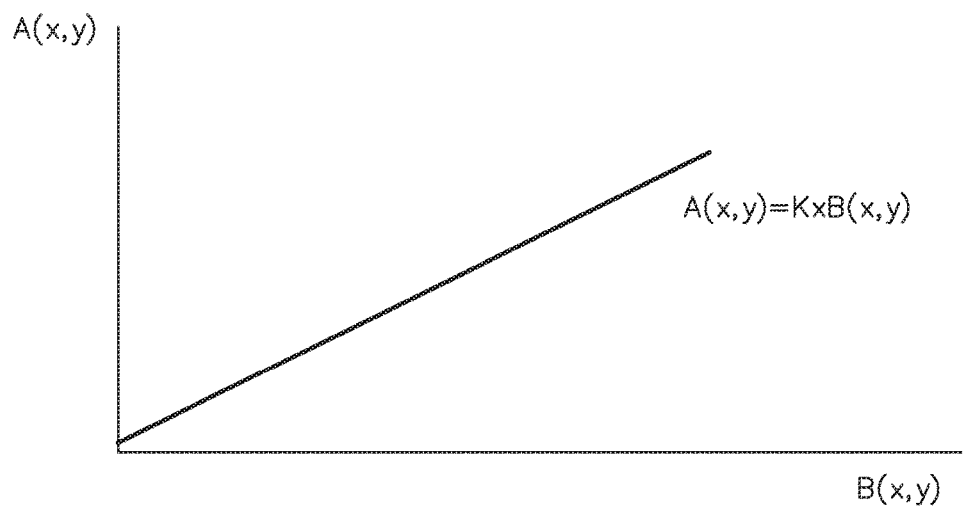
FIG. 12 is a graph showing a relationship between a gain and an offset according to one or more embodiments of the invention.

A modification may be configured to take images of the plurality of measurement reference areas 32 by radiation with different luminance levels. This is because the plurality of measurement reference areas 32 are not necessarily in the same color. As shown in FIG. 10, a modification may be configured to assign symbols such as U1 to U5 to the respective measurement reference areas 32 in display of type information and to allow the background luminance to be set corresponding to each of the measurement reference areas 32. For example, an entry field 35 is provided corresponding to the signs displayed in the image PG2 of the printed circuit board 1.

(h) The embodiments described above are configured to correct the soldering luminance with the ratio of the average value of luminance of the background area in the image data to the target value. This configuration causes the soldering luminance to be corrected by a relatively simple mathematical expression. The actual luminance and the luminance of the image data are, however, not completely linearly proportional to each other.

According to a modification, correction information may be stored in advance in the database 27. The correction information may be, for example, a correction factor of the soldering luminance according to the average value of luminance in the background area. Upon determination that it is impossible to perform three-dimensional measurement of the measurement reference area 32 based on imaging with the first light pattern, the background luminance is set by referring to this correction information and correcting the soldering luminance. This ensures the more appropriate setting of the background luminance and enables three-dimensional measurement of the measurement reference area 32 to be reliably performed by imaging with the background luminance.

(i) The configuration of the above embodiment has prominent advantageous effects when the measurement reference area 32 (background area) is in black or in gray relatively close to black as described above. When the measurement reference area 32 (background area) is in white or in gray relatively close to white, the image data taken with the luminance corresponding to the inspection object area 31 (solder area) is more likely to give an excessively high luminance in the measurement reference area 32 (background area) and cause saturation. Accordingly, the configuration also has prominent advantageous effects when the measurement reference area 32 (background area) is in white or in gray relatively close to white.

Although the disclosure has been described with respect to only a limited number of embodiments, those skilled in the art, having benefit of this disclosure, will appreciate that various other embodiments may be devised without departing from the scope of the present invention. Accordingly, the scope of the should be limited only by the attached claims.

REFERENCE SIGNS LIST

1 . . . printed circuit board, 2 . . . base substrate, 3 . . . electrode pattern, 4 . . . solder paste, 5 . . . resist film, 8 . . . substrate inspection apparatus, 10 . . . illumination device, 10a . . . light source, 10b . . . liquid crystal grid, 11 . . . camera, 12 . . . control device, 24 . . . data storage device, 25 . . . three-dimensional arithmetic device, 26 . . . inspection result storage device, 27 . . . database, 27A . . . soldering table, 27B . . . substrate table, 31 . . . inspection object area, 32 . . . measurement reference area, $A_1$, $A_2$ . . . gains, $B_1$, $B_2$ . . . offsets, K . . . proportional constant

What is claimed is:

1. A three-dimensional measurement device, comprising:
   an irradiator that:
   comprises a light source that emits a predetermined light and a grid that converts the light from the light source into a light pattern having a striped light intensity distribution; and
   irradiates a measurement object comprising at least a first and a second measurement object area with the light pattern;
   a luminance controller that changes luminance levels of the light emitted from the light source;
   a phase controller that controls transfer or changeover of the grid and that changes phase levels of the light pattern radiated from the irradiator;
   a camera that takes an image of reflected light from the measurement object irradiated with the light pattern; and
   a processor that:
   performs three-dimensional measurement of the first measurement object area based on a predetermined number of different image data taken by radiating a first light pattern of a first luminance level corresponding to the first measurement object area in a predetermined number of different phases;
   determines a relationship between a gain and an offset determined according to a predetermined imaging condition based on the predetermined number of different image data taken under the first light pattern; and
   performs three-dimensional measurement of the second measurement object area based on two different image data taken by radiating a second light pattern of a second luminance level corresponding to the second measurement object area in two different phases by using values of a gain and an offset with respect to each pixel determined according to a luminance value of each pixel in the two different image data and the determined relationship.

2. The three-dimensional measurement device according to claim 1, wherein the relationship between the gain and the offset is a relationship that mutually and unequivocally determines the gain and the offset.

3. The three-dimensional measurement device according to claim 2, wherein the processor calculates a phase θ that satisfies relations of Expressions (1), (2) and (3) given below in measurement of the second measurement object area:

$$V_0 = A \sin \theta + B \tag{1}$$

$$V_1 = A \sin(\theta+\gamma) + B \tag{2}$$

$$A = KB \tag{3}$$

where $V_0$ and $V_1$ respectively denote luminance values of each pixel in the two different image data when the second light pattern changes the phase in the two different phases that are respectively expressed as relative phases of θ and γ, γ≠0, A denotes the gain, B denotes the offset and K denotes a proportional constant.

4. The three-dimensional measurement device according to claim 3, wherein Y is equal to 90 degrees or is equal to 180 degrees.

5. The three-dimensional measurement device according to claim 4, wherein one of the first measurement object area and the second measurement object area is an inspection object area, and the other is a measurement reference area.

6. The three-dimensional measurement device according to claim 3, wherein one of the first measurement object area and the second measurement object area is an inspection object area, and the other is a measurement reference area.

7. The three-dimensional measurement device according to claim 2, wherein one of the first measurement object area and the second measurement object area is an inspection object area, and the other is a measurement reference area.

8. The three-dimensional measurement device according to claim 1, wherein the relationship between the gain and the offset is a relationship that gives the gain and the offset proportional to each other.

9. The three-dimensional measurement device according to claim 8, wherein the processor calculates a phase θ that satisfies relations of Expressions (1), (2) and (3) given below in measurement of the second measurement object area:

$$V_0 = A \sin \theta + B \tag{1}$$

$$V_1 = A \sin(\theta+\gamma) + B \tag{2}$$

$$A = KB \tag{3}$$

where $V_0$ and $V_1$ respectively denote luminance values of each pixel in the two different image data when the second light pattern changes the phase in the two different phases that are respectively expressed as relative phases of θ and γ, γ≠0, A denotes the gain, B denotes the offset and K denotes a proportional constant.

10. The three-dimensional measurement device according to claim 9, wherein Y is equal to 90 degrees or is equal to 180 degrees.

11. The three-dimensional measurement device according to claim 10, wherein one of the first measurement object area and the second measurement object area is an inspection object area, and the other is a measurement reference area.

12. The three-dimensional measurement device according to claim 9, wherein one of the first measurement object area and the second measurement object area is an inspection object area, and the other is a measurement reference area.

13. The three-dimensional measurement device according to claim 8, wherein one of the first measurement object area and the second measurement object area is an inspection object area, and the other is a measurement reference area.

14. The three-dimensional measurement device according to claim 1, wherein the processor calculates a phase θ that satisfies relations of Expressions (1), (2) and (3) given below in measurement of the second measurement object area:

$$V_0 = A \sin \theta + B \quad (1)$$

$$V_1 = A \sin(\theta + \gamma) + B \quad (2)$$

$$A = KB \quad (3)$$

where $V_0$ and $V_1$ respectively denote luminance values of each pixel in the two different image data when the second light pattern changes the phase in the two different phases that are respectively expressed as relative phases of θ and γ, γ≠0, A denotes the gain, B denotes the offset and K denotes a proportional constant.

15. The three-dimensional measurement device according to claim 14, wherein Y is equal to 90 degrees or is equal to 180 degrees.

16. The three-dimensional measurement device according to claim 15, wherein one of the first measurement object area and the second measurement object area is an inspection object area, and the other is a measurement reference area.

17. The three-dimensional measurement device according to claim 14, wherein one of the first measurement object area and the second measurement object area is an inspection object area, and the other is a measurement reference area.

18. The three-dimensional measurement device according to claim 1, wherein one of the first measurement object area and the second measurement object area is an inspection object area, and the other is a measurement reference area.

19. The three-dimensional measurement device according to claim 1, wherein the measurement object is either a printed circuit board with solder paste printed thereon or a wafer substrate with a solder bump formed thereon.

20. A three-dimensional measurement method using a three-dimensional measurement device that comprises an irradiator, a luminance controller, a phase controller, a camera, and a processor, wherein the irradiator comprises a light source that emits a predetermined light and a grid that converts the light from the light source into a light pattern having a striped light intensity distribution, the method comprising:

irradiating, by the irradiator, a measurement object comprising at least a first and a second measurement object area with the light pattern;

changing, by the luminance controller, luminance levels of the light emitted from the light source;

controlling, by the phase controller, transfer or changeover of the grid and changing phase levels of the light pattern radiated from the irradiator;

taking, by the camera, an image of reflected light from the measurement object irradiated with the light pattern;

performing, by the processor, three-dimensional measurement of the first measurement object area based on a predetermined number of different image data taken by radiating a first light pattern of a first luminance level corresponding to the first measurement object area in a predetermined number of different phases;

determining, by the processor, a relationship between a gain and an offset determined according to a predetermined imaging condition based on the predetermined number of different image data taken under the first light pattern; and performing, by the processor, three-dimensional measurement of the second measurement object area based on two different image data taken by radiating a second light pattern of a second luminance level corresponding to the second measurement object area in two different phases by using values of a gain and an offset with respect to each pixel determined according to a luminance value of each pixel in the two different image data and the determined relationship.

* * * * *